US012797112B2

(12) United States Patent
Chavez-Badiola et al.

(10) Patent No.: US 12,797,112 B2
(45) Date of Patent: Nov. 17, 2026

(54) EGG PREPARATION SYSTEM IN AN INTELLIGENT AUTOMATED FERTILITY PLATFORM

(71) Applicant: Conceivable Life Sciences Inc., New York, NY (US)

(72) Inventors: Alejandro Chavez-Badiola, Mexico City (MX); Alan Murray, Greenwich, CT (US); Jacques Cohen, New York, NY (US); Gerardo Mendizabal-Ruiz, Guadalajara (MX)

(73) Assignee: Conceivable Life Sciences Inc., New York, NY (US)

( * ) Notice: Subject to any disclaimer, the term of this patent is extended or adjusted under 35 U.S.C. 154(b) by 0 days.

(21) Appl. No.: 19/447,265

(22) Filed: Jan. 13, 2026

(65) Prior Publication Data

US 2026/0137422 A1 May 21, 2026

Related U.S. Application Data

(63) Continuation-in-part of application No. 19/180,598, filed on Apr. 16, 2025, which is a continuation of (Continued)

(51) Int. Cl.

| | |
|---|---|
| ***A61B 17/43*** | (2006.01) |
| ***A61B 3/10*** | (2006.01) |

(Continued)

(52) U.S. Cl.

CPC .............. *A61B 17/43* (2013.01); *A61B 3/102* (2013.01); *A61B 3/14* (2013.01); *A61B 5/0066* (2013.01);

(Continued)

(58) Field of Classification Search

None

See application file for complete search history.

(56) References Cited

U.S. PATENT DOCUMENTS

| | | | |
|---|---|---|---|
| 6,608,717 | B1 | 8/2003 | Medford |
| 11,494,578 | B1 | 11/2022 | Chian |

(Continued)

FOREIGN PATENT DOCUMENTS

| | | | |
|---|---|---|---|
| CN | 112401994 | A | 2/2021 |
| WO | 0004929 | A1 | 2/2000 |

(Continued)

OTHER PUBLICATIONS

Zhu et al. "Study of Robotic System for Automated Oocyte Manipulation" (2017), IEEE, 2017 Intern'l Conf on Manipulation, Automation, and Robotics at Small Scales (MARSS).

(Continued)

*Primary Examiner* — Phuoc Tran

(74) *Attorney, Agent, or Firm* — Miller Johnson

(57) ABSTRACT

A system for automated, artificial intelligence based oocyte identification and processing includes an imaging system, a set of stations, a set of robotic arms, and an artificial intelligence/machine learning system. The imaging system is positioned in proximity to a biological sample containing a candidate cumulus oocyte complex. The imaging system is configured to identify and locate the candidate cumulus oocyte complex within the biological sample. Each station of the set of stations is configured to receive the biological sample. The set of robotic arms is configured to move the biological sample between one or more stations of the set of stations and denude the candidate cumulus oocyte complex from the biological sample. The artificial intelligence/ma- (Continued)

chine learning system is operatively coupled to at least one of: the imaging system, the set of robotic arms, or the set of stations.

19 Claims, 11 Drawing Sheets

Related U.S. Application Data application No. 18/431,259, filed on Feb. 2, 2024, now Pat. No. 12,310,625, which is a continuation of application No. PCT/US2024/013428, filed on Jan. 30, 2024.

(60) Provisional application No. 63/523,258, filed on Jun. 26, 2023.

(51) Int. Cl.

| | |
|---|---|
| ***A61B 3/14*** | (2006.01) |
| ***A61B 5/00*** | (2006.01) |
| ***A61B 17/425*** | (2006.01) |
| ***A61B 34/30*** | (2016.01) |
| ***A61B 34/37*** | (2016.01) |
| ***B25J 9/16*** | (2006.01) |
| ***C12M 1/00*** | (2006.01) |
| ***C12M 1/02*** | (2006.01) |
| ***C12M 1/22*** | (2006.01) |
| ***C12M 1/26*** | (2006.01) |
| ***C12M 1/36*** | (2006.01) |
| ***C12M 3/00*** | (2006.01) |
| ***C12N 5/073*** | (2010.01) |
| ***G01N 33/50*** | (2006.01) |
| ***G01N 35/00*** | (2006.01) |
| ***G01N 35/10*** | (2006.01) |
| ***G06T 7/20*** | (2017.01) |
| ***G06T 7/70*** | (2017.01) |
| ***G06V 10/82*** | (2022.01) |
| ***G06V 20/69*** | (2022.01) |
| *A61B 34/32* | (2016.01) |

(52) U.S. Cl.

CPC ............ *A61B 17/425* (2013.01); *A61B 34/30* (2016.02); *A61B 34/37* (2016.02); *B25J 9/1602* (2013.01); *C12M 21/06* (2013.01); *C12M 23/10* (2013.01); *C12M 23/48* (2013.01); *C12M 23/50* (2013.01); *C12M 33/04* (2013.01); *C12M 41/06* (2013.01); *C12M 41/18* (2013.01); *C12M 41/48* (2013.01); *C12N 5/0604* (2013.01); *G01N 33/5091* (2013.01); *G01N 35/0099* (2013.01); *G01N 35/10* (2013.01); *G01N 35/1011* (2013.01); *G06T 7/20* (2013.01); *G06T 7/70* (2017.01); *G06V 10/82* (2022.01); *G06V 20/693* (2022.01); *A61B 34/32* (2016.02); *G06T 2207/20081* (2013.01); *G06T 2207/30024* (2013.01); *G06V 20/69* (2022.01); *G06V 20/698* (2022.01); *G06V 2201/03* (2022.01)

(56) References Cited

U.S. PATENT DOCUMENTS

2012/0283125 A1* 11/2012 Sirard .................. G01N 33/689 435/6.12
2013/0337487 A1 12/2013 Loewke
2014/0297199 A1 10/2014 Osten
2015/0252328 A1 9/2015 Woodruff
2017/0140535 A1 5/2017 Hamamah
2017/0205390 A1 7/2017 Shaked
2020/0305967 A1 10/2020 Getman
2021/0396776 A1* 12/2021 Lapham ............. G01N 35/1016
2022/0156922 A1 5/2022 Chávez Badiola
2022/0189640 A1 6/2022 Wessels Wells
2022/0260826 A1 8/2022 Moore
2022/0328188 A1 10/2022 Sanchez
2022/0358655 A1 11/2022 Wessels Wells
2023/0093989 A1 3/2023 Mahajan
2023/0303959 A1 9/2023 Blanchard
2024/0418370 A1* 12/2024 Kramme ............... F04D 29/545
2024/0426812 A1* 12/2024 Chavez-Badiola .... A61B 17/43

FOREIGN PATENT DOCUMENTS

WO 2016001754 A2 1/2016
WO 2021014461 A1 1/2021
WO 2021160347 A1 8/2021

OTHER PUBLICATIONS

Abdullah et al., "Automation in ART: Paving the Way for the Future of Infertility Treatment," Published online Aug. 2022, Reproductive Sciences, vol. 30: 1006-1016.

Casciani et al., "Are we approaching automated assisted reproductive technology? Sperm analysis oocyte manipulation, and insemination," Fertil Steril, vol. 2, No. 3: 189-203, 2021.

Trottmann, et al., "Ex vivo investigations on the potential of optical coherence tomography (OCT) as a diagnostic tool for reproductive medicine in a bovine model," vol. 9, No. 1-2: 129-137, 2016.

Fan, et al., "Optimized Optical Coherence Tomography Imaging with Hough Transform-Based Fixed-Pattern Noise Reduction," IEEE Access, vol. 6, 32087-32096, 2018.

Zhai, et al., "Automated Denudation of Oocytes," Micromachines, 2022.

Targosz, et al., "Semantic segmentation of human oocyte images using deep neural networks," BioMedical Engineering, 20:40, 2021.

Zhai et al., "Automated Denudation of Oocytes," Micromachines, 2022, 14 pages.

International Search Report and Written Opinion of the International Searching Authority issued for PCT/US24/13428, mad Aug. 2, 2024, 22 pages.

Costa-Borges, et al., "First babies conceived with Automated Intracytoplasmic Sperm Injection," May 24, 2023, retrieved Nov. 8, 2024, <https://www.rbmojournal.com/article/S1472-6483(23)00335-8/fulltext>. 12 pages.

Martin et al., "Positive rheotaxis extended drop: a one-step procedure to select and recover sperm with mature chromatin for intracytoplasmic sperm injection," published Sep. 19, 2017, DOI 10.1007/s10815-017-1024-1. 10 pages.

Baldini et al., "A fast and safe technique for sperm preparation in ICSI treatments within a randomized controlled trial (RCT)," Reproductive Biology and Endocrinology 18:88, <https://doi.org/10.1186/s12958-020-00642-8>, published Aug. 19, 2020. 9 pages.

* cited by examiner

EGG PREPARATION SYSTEM IN AN INTELLIGENT AUTOMATED FERTILITY PLATFORM

CROSS-REFERENCE TO RELATED APPLICATIONS

This application is a continuation-in-part of U.S. application Ser. No. 19/180,598 filed Apr. 16, 2025, which is a continuation of U.S. application Ser. No. 18/431,259 filed Feb. 2, 2024 (now U.S. Pat. No. 12,310,625), which is a continuation of PCT International Application No. PCT/US2024/013428 filed Jan. 30, 2024, which claims the benefit of U.S. Provisional Application No. 63/523,258 filed Jun. 26, 2023. The entire disclosures of the above applications are incorporated by reference.

FIELD

The present disclosure relates to fertility treatment automation and preparation and more particularly to automated robotic preparation of materials and biological samples for use in fertility procedures such as in vitro fertilization and intracytoplasmic sperm injection.

BACKGROUND

Traditional in vitro fertilization (IVF) technologies have largely depended on the assistance of human clinical embryologists and/or andrologists to perform, evaluate, and/or respond to the requirements of IVF processes. This has resulted in expensive IVF intervention that limits access to IVF due to economic constraints, geographic and other limitations, and which is subject to the vagaries of human performance and inconsistencies across clinical settings, equipment, and expertise. Employing methods and systems for the use of intelligent, automated systems of interconnected robotic IVF modules, including intracytoplasmic sperm injection (ICSI) techniques which can be supported by imaging, artificial intelligence/machine learning (AI/ML), and robotic automation processes, for obtaining, storing, analyzing, performing, and reporting on a plurality of materials, data, processes, actions, and outcomes relating to IVF/ICSI—can improve accessibility and affordability of IVF interventions.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A system for automated, artificial-intelligence-based oocyte identification and processing includes an imaging system, a set of stations, a set of robotic arms, and an artificial intelligence/machine learning system (AI/ML system). The imaging system is positioned in proximity to a biological sample containing a potential cumulus oocyte complex (COC). The imaging system is configured to identify and locate the potential COC within the biological sample. Each station of the set of stations is configured to receive the biological sample. The set of robotic arms is configured to move the biological sample between one or more stations of the set of stations and denude the potential COC from the biological sample. The AI/ML system is operatively coupled to at least one of: the imaging system, the set of robotic arms, or the set of stations.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

System

Figure 1:
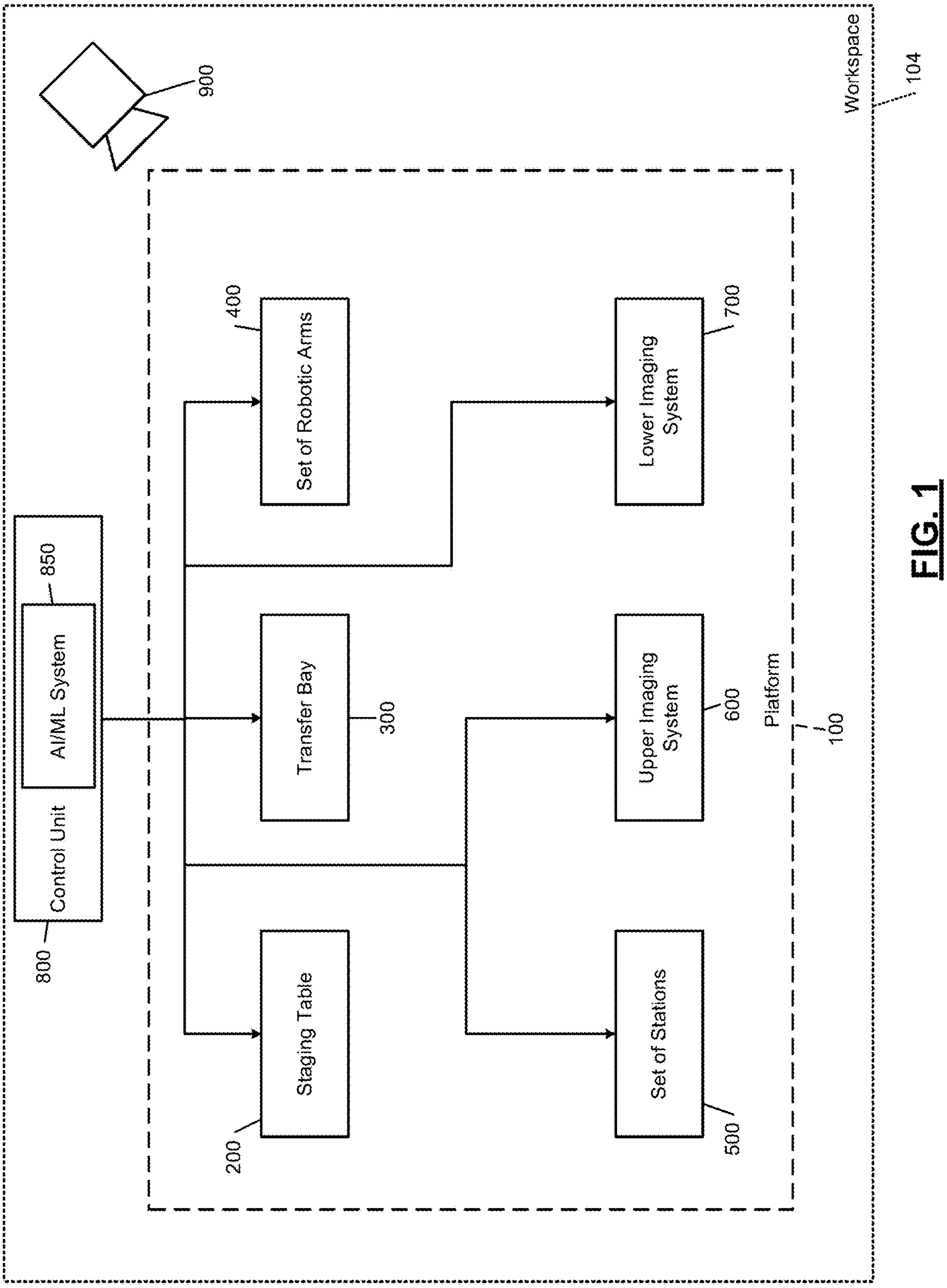
FIG. 1 is a block diagram of an egg preparation platform in an enclosed workspace according to the principles of the present disclosure.
Figure 2:
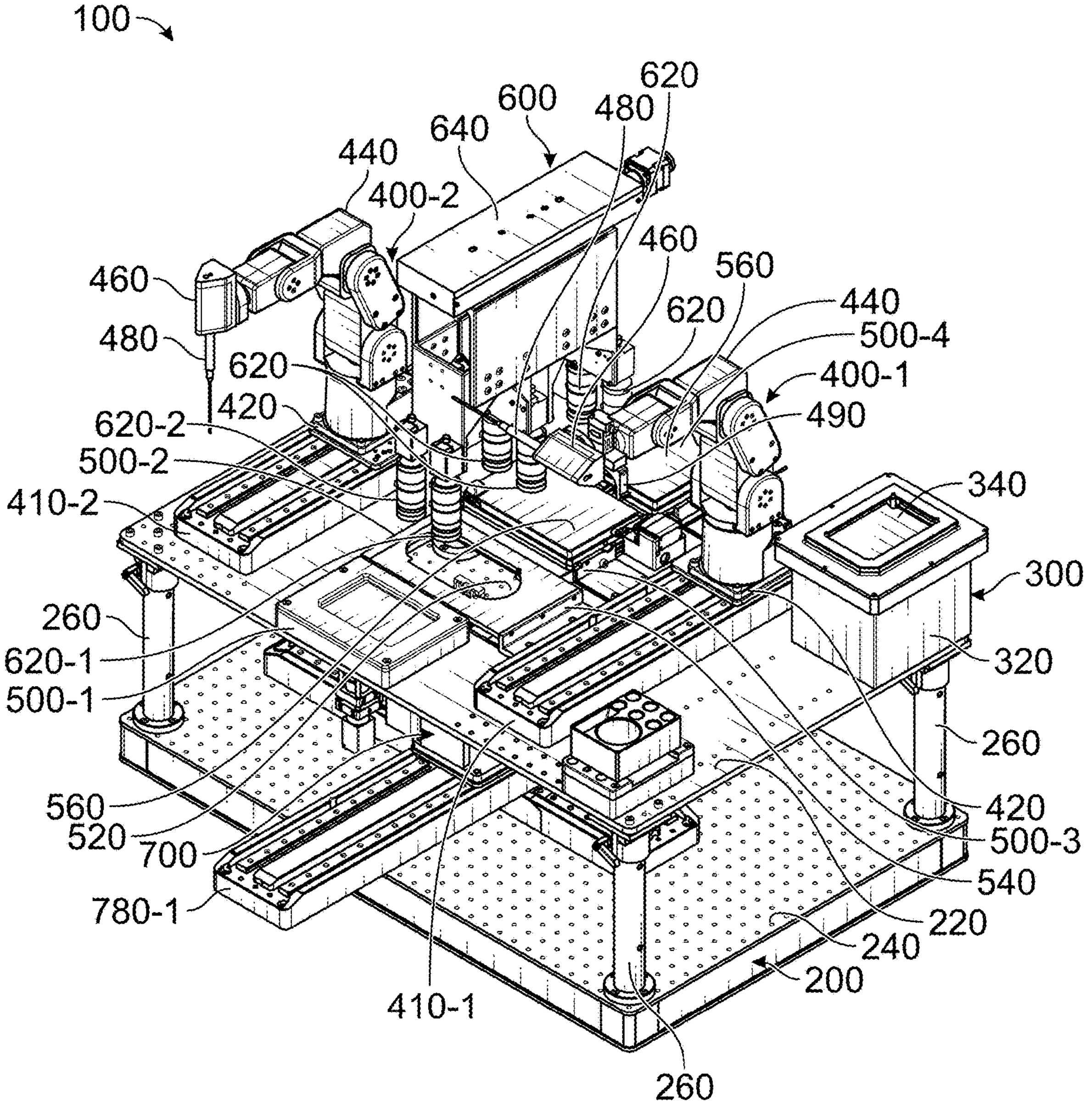
FIG. 2 is a perspective view of the platform of FIG. 1.
Figure 3:
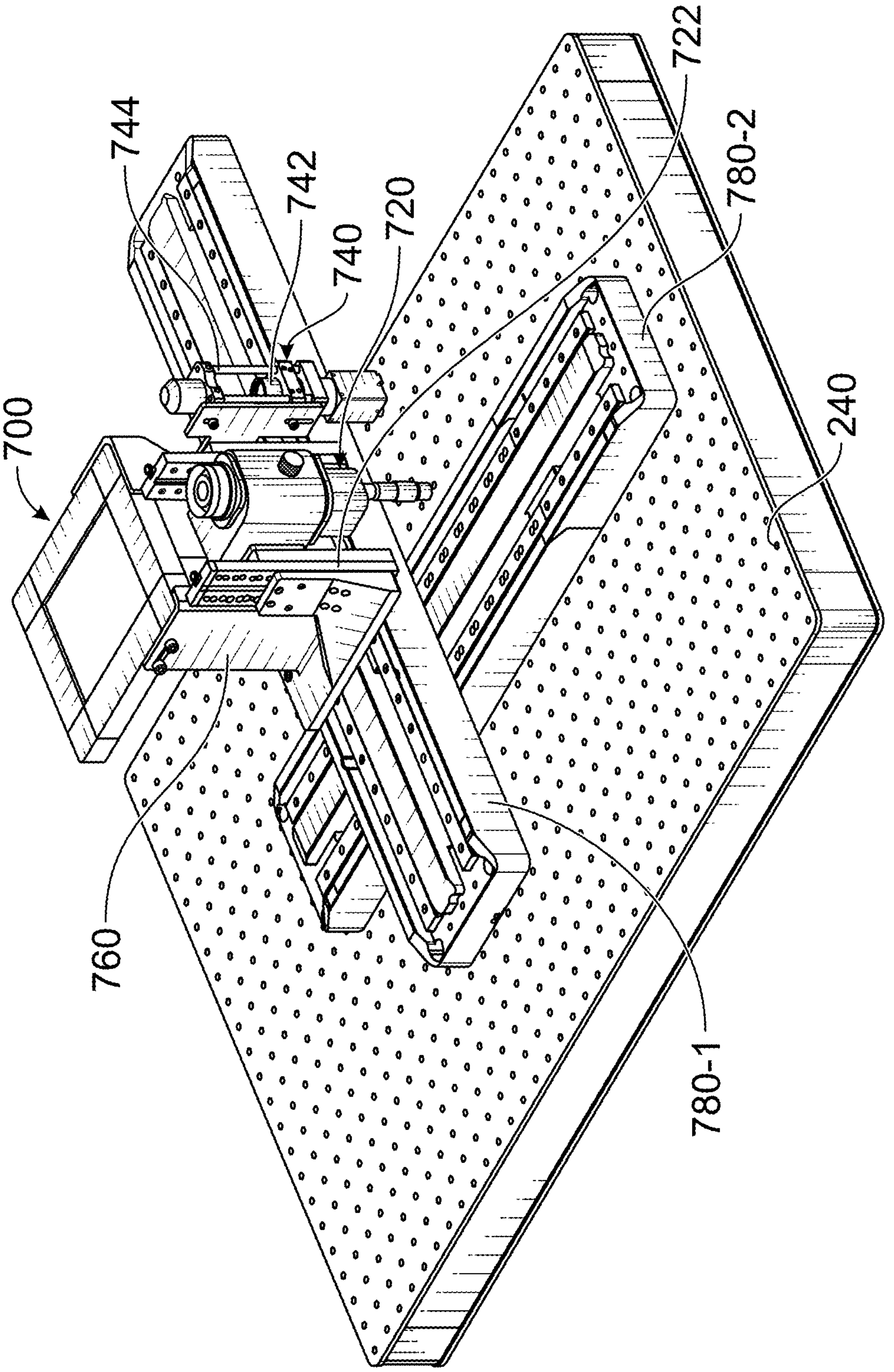
FIG. 3 is a perspective view of a lower imaging system of the platform of FIG. 1.
Figure 4:
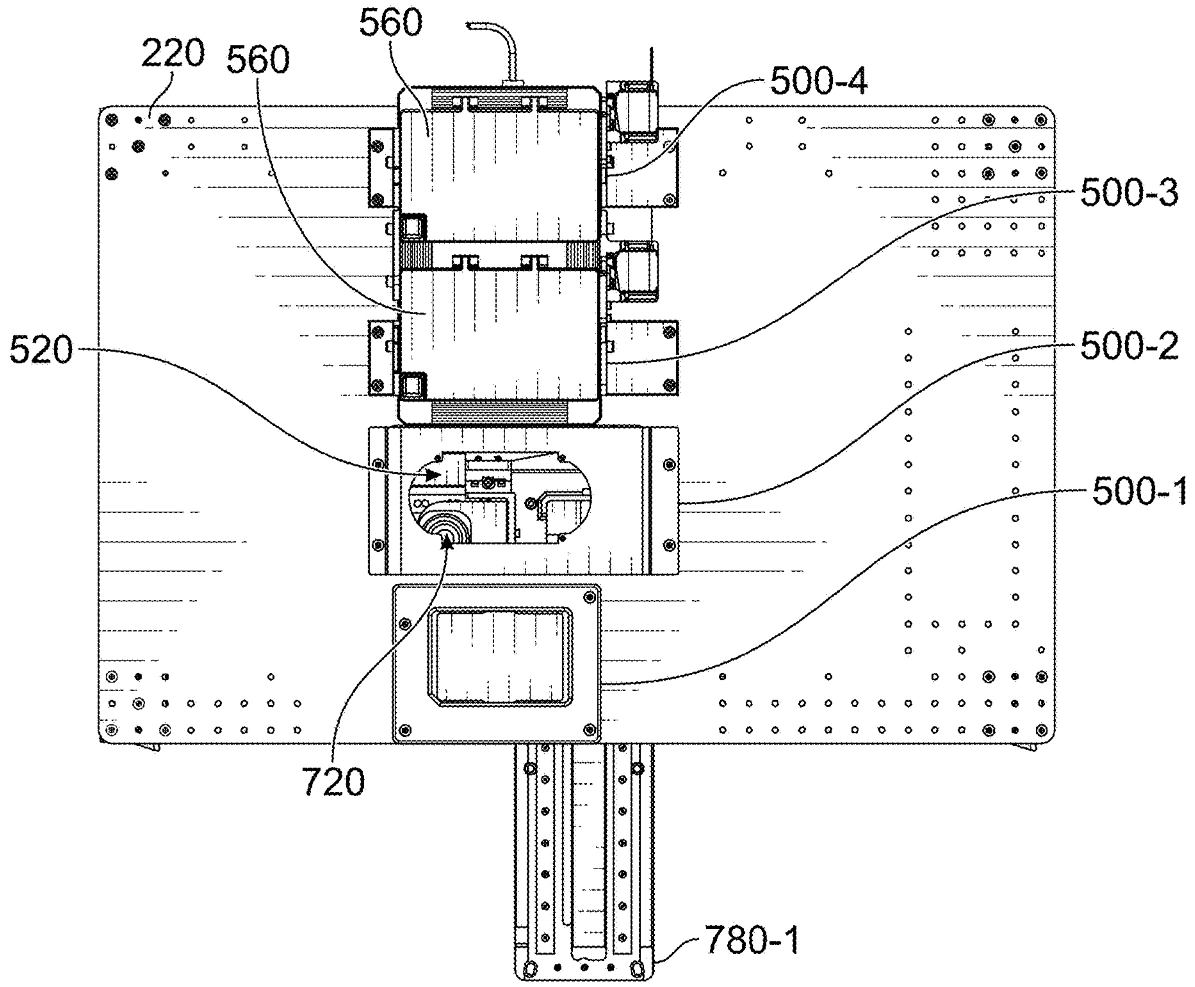
FIG. 4 is a top view of the platform of FIG. 1.

FIGS. 1-4 illustrate a platform 100 configured to prepare eggs, such as for use with in vitro fertilization (IVF) and/or intracytoplasmic sperm injection (ICSI) processes. As described in more detail below, the platform 100 (also referred to as an egg preparation platform) may prepare an egg with minimal or no human intervention specifically, the platform 100 may use artificial intelligence, machine learning, and/or robotics to automate the egg preparation process. The platform 100 may reduce or eliminate mistakes or errors in the egg preparation process that are traditionally introduced by humans, thereby increasing the percentage of successful IVF/ICSI procedures. Use of the platform 100 may reduce the costs associated with egg preparation, thereby increasing the access to IVF/ICSI processes to more people. Further, the platform 100 may replace multiple different parts, stations, and machines traditionally needed to perform the egg preparation process, thereby decreasing the overall amount of space and time needed to perform the egg preparation process. In various implementations, the platform 100 may also perform various other IVF/ICSI processes, such as sperm preparation and sperm injection, among others: as a result, the platform 100 may also be referred to as an IVF/ICSI platform.

The platform 100 may include a staging table 200, a transfer bay 300, a set of robotic arms 400, a set of stations 500, an upper imaging system 600, and a lower imaging system 700. The platform 100 may be contained within a workspace 104, which may be at least partially enclosed to allow for environmental control for the platform 100. In various implementations, the workspace 104 is a room, which may provide a controlled environment for the platform 100, as well as other systems or workstations.

In various implementations, the platform 100 includes and is electronically coupled with a control unit 800 that controls various components of the platform 100. In various implementations, the control unit 800 includes an artificial intelligence/machine learning (AI/ML) system 850. The AI/MVL system 850 may control one or more of the components of the platform 100 including, but not limited to, the set of robotic arms 400, the upper imaging system 600, or the lower imaging system 700.

Staging Table

The staging table 200 may include a top plate 220, a bottom plate 240 spaced apart from the top plate 220, and multiple legs 260 connecting the top plate 220 and the bottom plate 240. In various implementations, one or both of the top plate 220 and the bottom plate 240 are rectangular in shape. In various implementations, one or more components of the platform 100 are disposed on the top plate 220 or the bottom plate 240. For example, in various implementations, the transfer bay 300, the set of robotic arms 400, the set of stations 500, and the upper imaging system 600 are disposed on the top plate 220 and the lower imaging system 700 is disposed on the bottom plate 240. In various implementations, the one or more components of the platform 100 are connected to the staging table 200, such as by mechanical fasteners, adhesives, welding, or other securement measures.

In various implementations, the staging table 200 includes passive dampening elements that reduce vibration transmitted from the surrounding environment to the components of the platform 100. In various implementations, the passive dampening elements completely isolate the components of the platform 100 from vibrations from the surrounding environment. The passive dampening elements may be a part of, or coupled to, the legs 260, the bottom plate 240, and/or the top plate 220. The passive dampening elements may be any suitable type of vibration dampener, examples of which include resilient portions, springs, rubber connectors or feet, etc. In various implementations, the anti-vibration provided by the passive dampening elements improves the functionality of the upper imaging system 600 and/or the lower imaging system 700.

Transfer Bay

The transfer bay 300 may be disposed in a corner of the top plate 220. The transfer bay 300 may include a raised platform 320 and a dish holder 340 disposed on top of the raised platform 320. The dish holder 340 may receive, and temporarily store, one or more carriers 1000 (FIG. 5 to be used within the platform 100. As will be discussed in more detail below, the one or more carriers 1000 may be removed from an external incubator (not shown) and placed in the dish holder 340 by a human operator or external automated system (not shown). When the one or more carriers 1000 are disposed in the dish holder 340, an external device 900 (such as a camera, laser scanner, etc.) may be used to verify the identity of the carrier 1000. As will be discussed in more detail below, the set of robotic arms 400 may remove the carrier 1000 from the dish holder 340 and transfer it around the platform 100.

In various implementations, the transfer bay 300 includes a backlight, such as a collimated backlight, disposed in the raised platform 320. The backlight may illuminate the one or more carriers 1000. In various implementations, the transfer bay 300 is temperature and/or environmentally controlled. In various implementations, the height of the raised platform 320 is chosen such that the one or more carriers 1000 are placed at an optimal height to be grabbed by the set of robotic arms 400.

Figure 5:
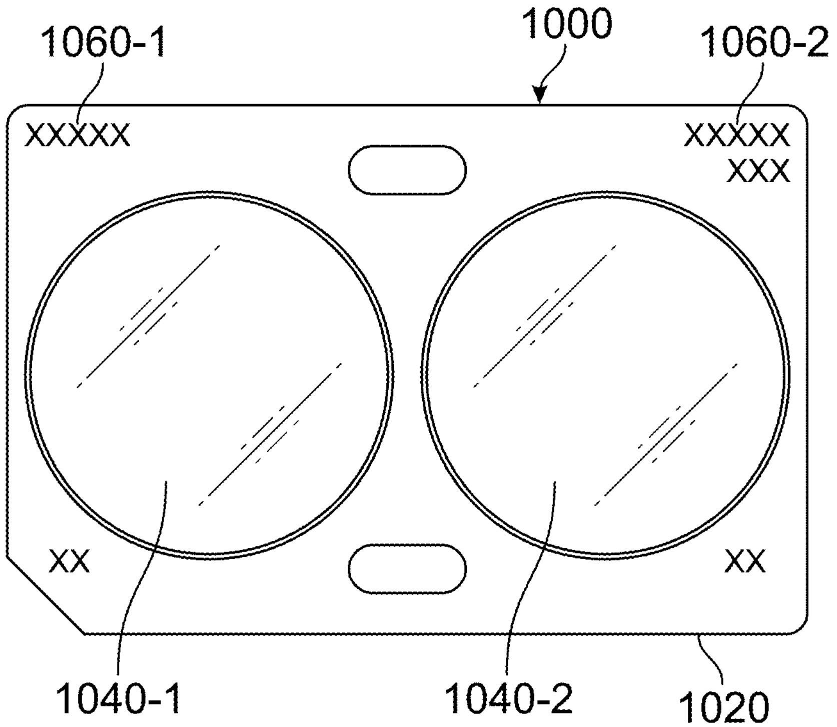
FIG. 5 is a top view of a carrier for culture containers according to the principles of the present disclosure.

FIG. 5 illustrates an example carrier 1000 for use within the platform 100. While the carrier 1000 is illustrated as a carrier plate, the carrier 1000 can have any suitable shape or structure, such that it is compatible for interaction with the set of robotic arms 400, the dish holder 340, and/or the set of stations 500. In various implementations, the carrier 1000 includes a carrier body 1020 defining a set of container seats 1040. In the example of FIG. 5, the set of container seats 1040 includes a first container seat 1040-1 and a second container seat 1040-2.

Figure 6:
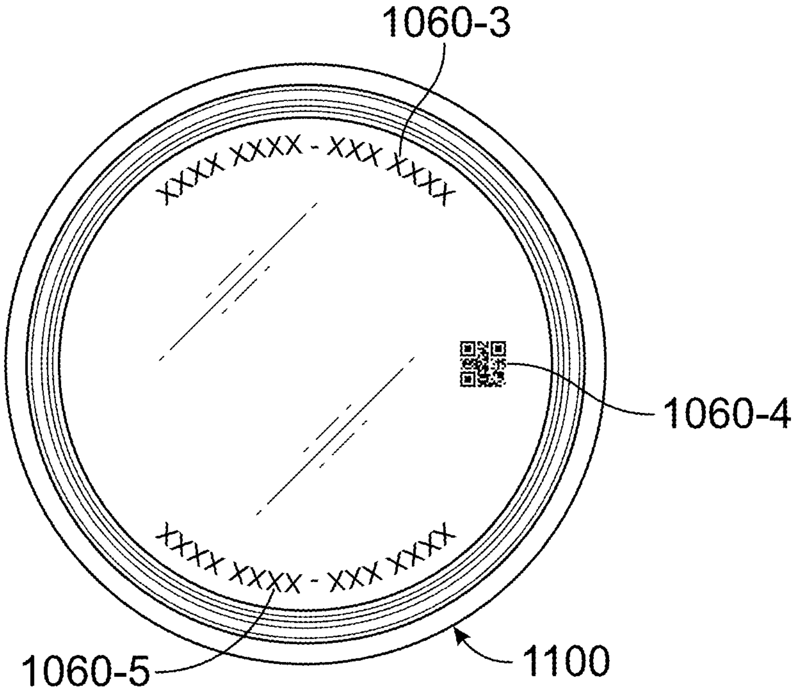
FIG. 6 is a top view of the culture container for receipt by the carrier of FIG. 5 according to the principles of the present disclosure.

Each of the set of container seats 1040 is configured to receive a culture container 1100 (FIG. 6). While the culture containers 1100 are illustrated as culture dishes, any container suitable for receiving and/or conveying a sample or a culture may be provided, examples of which include culture dishes, such as petri dishes, slides, culture plates, etc. While the carrier 1000 is illustrated as receiving two culture containers, the carrier 1000 may receive a single culture container or more than two culture containers. In various implementations, the one or more carriers 1000 are omitted and the one or more culture containers 1100 are used without a corresponding carrier. In various implementations, each of the one or more culture containers 1100 include one or more wells within the culture container 1100. Each well may be a subdivided portion of the culture container 1100 that is separate from the rest of the culture container. As will be described in more detail below, various operations on the biological sample may be performed in different wells of the same culture container.

The carrier 1000 may also include one or more identifiers providing information relating to the carrier 1000. For example, the identifiers may include text defining a lot number or a part number of the carrier 1000, an identifier such as a barcode or an identification number, and/or may include information relating to the identification of the specific sample or culture being carried by the carrier 1000, which may likewise be in text form or in the form of a bar code or a QR code. In various implementations, each of the culture containers 1100 may also include one or more identifiers. As an example only, FIG. 5 depicts the carrier 1000 with a first identifier 1060-1 and a second identifier 1060-2. As another example, FIG. 6 shows the culture container 1100 with a first identifier 1060-3, a second identifier 1060-4, and a third identifier 1060-5.

The carrier 1000 and/or culture container 1100 may contain one or more biological samples, upon which the egg preparation process and/or various other IVF/ICSI processes may be performed by the platform 100. A biological sample may include multiple cumulus masses surrounded by follicular fluid. A cumulus mass is a clump of cumulus cells. One or more of the plurality of cumulus masses may also contain an oocyte (an immature egg). A cumulus mass that contains an oocyte is a Cumulus-Oocyte Complex (COC). In this regard, each of the cumulus masses may be referred to as a potential COC because each cumulus mass may or not also be a COC depending on whether the cumulus mass contains an oocyte. The innermost layer of cumulus cells closest to the oocyte are referred to as corona cells. In various implementations, the platform 100 is configured to identify and extract (potential) COCs from a biological sample.

Set of Robotic Arms

In various implementations, the set of robotic arms 400 includes a first robotic arm 400-1 and a second robotic arm 400-2. While the set of robotic arms 400 is illustrated as having two robotic arms the set of robotic arms 400 may have a single robotic arm or more than two robotic arms. The first and second robotic arms 400-1, 400-2 may be located on the top plate 220 such that, collectively, the first and second robotic arms 400-1, 400-2 can interact with the transfer bay 300 and each of the set of stations 500. In various implementations, the set of robotic arms 400 is controlled by the control unit 800. In various implementations, the set of robotic arms 400 is controlled by the AI/ML system 850.

Each of the set of robotic arms 400 may include a base 420, an arm 440 extending from the base 420, and an end effector 460 attached to an end of the arm 440 opposite the base 420. The end effector 460 may receive and hold a tool 480 that is used to perform the egg preparation and/or various other IVF/ICSI processes. In various implementations, the tool 480 is a pipette. In various implementations, the pipette is a digitally controlled pipette that is interchangeably and magnetically attached to one of the set of robotic arms 400.

In various implementations, at least one of the set of robotic arms 400 includes a grabber 490 attached to the end effector 460. In various implementations, one of the set of robotic arms 400 can simultaneously hold the tool 480 and the grabber 490, while in other implementations, the tool 480 is detached before attaching the grabber 490.

Each of the set of robotic arms 400 may allow for six-axis movement, also referred to as six degrees of freedom. In various implementations, the set of robotic arms 400 is attached to a rail system that allows for translation of the set of robotic arms 400 in one dimension. In various implementations, the set of robotic arms 400 includes multiple robotic arms and the rail system allows for independent translation of each of the robotic arms. As an example, the first and second robotic arms 400-1, 400-2 are shown attached to respective rail systems 410-1 and 410-2, which allow for independent travel of the first and second robotic arms 400-1, 400-2 in one dimension.

Set of Stations

In various implementations, the set of stations 500 includes a first station 500-1, a second station 500-2, a third station 500-3, and a fourth station 500-4. While the set of stations 500 is illustrated as having four stations, the set of stations 500 may have more or fewer than four stations. As discussed in more detail below, the carrier 1000 may be moved between one or more of the set of stations 500 when performing the egg preparation process and/or various other IVF/ICSI processes. In various implementations, each of the set of stations 500 is set up such that a unique step (or steps) of the egg preparation process and/or various other IVF/ICSI processes is performed at each station. In various implementations, each of the set of stations 500 is identical and multiple (up to all) steps of the egg preparation process and/or various other IVF/ICSI processes are performed at each station.

In various implementations, work is performed in more than one of the set of stations 500 simultaneously. For example, the first robotic arm 400-1 may be working in the first station 500-1 while the second robotic arm 400-2 is working in the third station 500-3.

In various implementations, the first station 500-1 is a working station. In this regard, at various points throughout the various IVF/ICSI processes, the first station 500-1 may be used to wash the biological sample, extract various components from the biological sample using a pipette, or otherwise manipulate the biological sample. In various implementations, the first station 500-1 is temperature controlled. In various implementations, the first station 500-1 is maintained at a temperature of 37 degrees Fahrenheit.

In various implementations, the second station 500-2 is a viewing station. For example, the upper imaging system 600 and/or the lower imaging system 700 may view (for example, scan) the carrier 1000 and/or culture container 1100 to identify a biological sample (or components of the biological sample) within the carrier 1000 and/or culture container 1100.

In this regard, the second station 500-2 may have a transparent base plate 520 that allows the lower imaging system 700 to view the biological sample.

In various implementations, the third station 500-3 is a first incubator and the fourth station 500-4 is a second incubator. In various implementations, the third station 500-3 holds only unwashed eggs and the fourth station 500-4 holds eggs after denudation. Each of the third and fourth stations 500-3, 500-4 may include a main body 540 covered by a lid 560. In various implementations, opening and closing of the lid 560 is controlled by a servo motor. In various implementations, the lid 560 of the third and fourth stations 500-3, 500-4 does not form an airtight seal with the main body 540 to avoid over-pressurizing the third and fourth stations 500-3, 500-4.

Each of the third station 500-3 and the fourth station 500-4 may have a gas intake and various gases may be pumped into the third station 500-3 and the fourth station 500-4 to create a desired environment within the third station 500-3 and the fourth station 500-4. In various implementations, the gas intake is a valve that opens and closes to allow or restrict the flow of gases into the third station 500-3 or the fourth station 500-4. In various implementations, the desired environment is an environment ideal for incubation. In various implementations, the desired environment is a hypoxic environment (an environment with low levels of dissolved oxygen). In this regard, carbon dioxide and/or nitrogen may be pumped into the third station 500-3 or the fourth station 500-4 to create the hypoxic environment. In various implementations, the gases are homogenously disposed within the third station 500-3 or the fourth station 500-4. In various implementations, the gases maintain the pH of the culture medium.

Each of the third station 500-3 and the fourth station 500-4 may also be temperature controlled to assist in creating the desired environment. In various implementations, the temperature is the same (or substantially the same) in the third station 500-3 and the fourth station 500-4. In various implementations, both of the third station 500-3 and the fourth station 500-4 are kept at thirty-seven degrees Fahrenheit.

In various implementations, the lid 560 is digitally controlled for opening and closing. In various implementations, the lid 560 is controlled by the control unit 800. In various implementations, the lid 560 is controlled by the AI/ML system 850.

In various implementations, one or more backlights illuminate the third station 500-3 and/or the fourth station 500-4. In various implementations, the third station 500-3 and the fourth station 500-4 are illuminated by a single backlight simultaneously. In various implementations, the backlight is a collimated backlight. In various implementations, a visible light red spectrum filter is applied over the collimated backlight that filters out wavelengths that are harmful to eggs, such as wavelengths in the visible light red spectrum. In various implementations, the first station 500-1 and the second station 500-2 share a backlight (for example, a collimated backlight). In various implementations, the backlight illuminates only the first station 500-1 or the second station 500-2.

Upper Imaging System

The upper imaging system 600 may include a set of cameras 620 coupled to a carrier 640. The upper imaging system 600 may be disposed above the set of stations 500. In various implementations, the upper imaging system 600 is externally mounted (for example, to the ceiling of a room that the platform 100 is in). In various implementations, the upper imaging system 600 is connected to the staging table 200 (for example, by an arm that holds the upper imaging system 600 above the staging table 200). The upper imaging system 600 may be positioned such that it can view more than one of the set of stations 500 simultaneously. In various implementations, the upper imaging system 600 moves (translates) to view other stations of the set of stations 500 or to view other components (such as the transfer bay 300) of the platform 100. In various implementations, all of the set of cameras 620 move in unison along the carrier 640. In various implementations, a first subset of the set of cameras 620 are stationary and only a second subset of the set of cameras 620 move along the carrier 640. For example, only a first pair of the set of cameras 620 may move along the carrier 640. In various implementations, the upper imaging system 600 may need to move out of the way of the set of robotic arms 400 during performance of the egg preparation process and/or various other IVF/ICSI processes.

In various implementations, the set of cameras 620 includes six cameras. This may allow the set of cameras to view up to three stations of the set of stations 500 at any given time. In various implementations, the set of cameras 620 is arranged in a grid pattern having one or more rows and one or more columns. In various implementations, the set of cameras 620 is arranged in three rows of two cameras apiece. In various implementations, the number of cameras in each row is chosen based on the number of carriers that each station can hold and the number of culture dishes in each carrier. In one example, each of the set of stations 500 holds a single carrier and the carrier includes two culture dishes, so each row of the set of cameras 620 has two cameras. This allows each camera in the row to view a respective culture dish. In various implementations, each of the set of cameras 620 has a field of view that allows the camera to view the entirety of the culture dish without needing to move the camera or the culture dish. While the set of cameras 620 is illustrated as having six total cameras arranged in rows of two, the set of cameras 620 could have any number of cameras arranged in any arrangement. As explained in more detail below, the upper imaging system 600 may scan one or more biological samples to identify (potential) COCs.

Lower Imaging System

The lower imaging system 700 may include an optical coherence tomography (OCT) imaging system 720, a microscopy system 740, a base 760, a first track 780-1, and a second track 780-2. The OCT imaging system 720 and the microscopy system 740 may be coupled to the base 760. The base 760 may be translatably coupled to the first track 780-1 and the first track 780-1 may be translatably coupled to the second track 780-2. As discussed in more detail below, the OCT imaging system 720 and/or the microscopy system 740 may scan one or more biological samples to determine if an oocyte is present within a potential COC and/or to determine the maturity of an oocyte by detecting the presence or absence of a polar body. In various implementations, the OCT imaging system 720 scans one or more biological samples through the transparent base plate 520.

The OCT imaging system 720 may be movable in a first direction along a first guide 722. The first guide 722 may be coupled to the base 760. In various implementations, the first direction is a direction extending from the bottom plate 240 to the top plate 220. In various implementations, the first direction is perpendicular to the bottom plate 240 and/or the top plate 220. Movement of the OCT imaging system 720 in the first direction may be used to focus the OCT imaging system 720. In this regard, the first direction may be referred to as a linear focus axis for the OCT imaging system 720.

The microscopy system 740 may include a microscope 742 moveable in the first direction along a second guide 744. The second guide 744 may be coupled to the base 760. In various implementations, the microscope 742 may include a four times (4X) objective lens.

The base 760 may move (translate) along the first track 780-1 in a second direction. The second direction may be transverse to the first direction. In various implementations, the second direction is perpendicular to the first direction. In various implementations, the second direction is parallel to the bottom plate 240. The first track 780-1 may move (translate) along the second track 780-2 in a third direction. Movement of the first track 780-1 along the second track 780-2 also moves the base 760 in the third direction. The third direction may be transverse to the first direction and/or the second direction. In various implementations, the third direction is perpendicular to both the first direction and the second direction. In various implementations, the third direction is parallel to the bottom plate 240. Movement of the base 760 may be necessary in order for the OCT imaging system 720 and/or the microscopy system 740 to scan all of the potential COCs to determine if an oocyte is present.

Method

FIGS. 7-12 are flowcharts illustrating a method of operating the platform 100 for preparing an egg.

Figure 7:
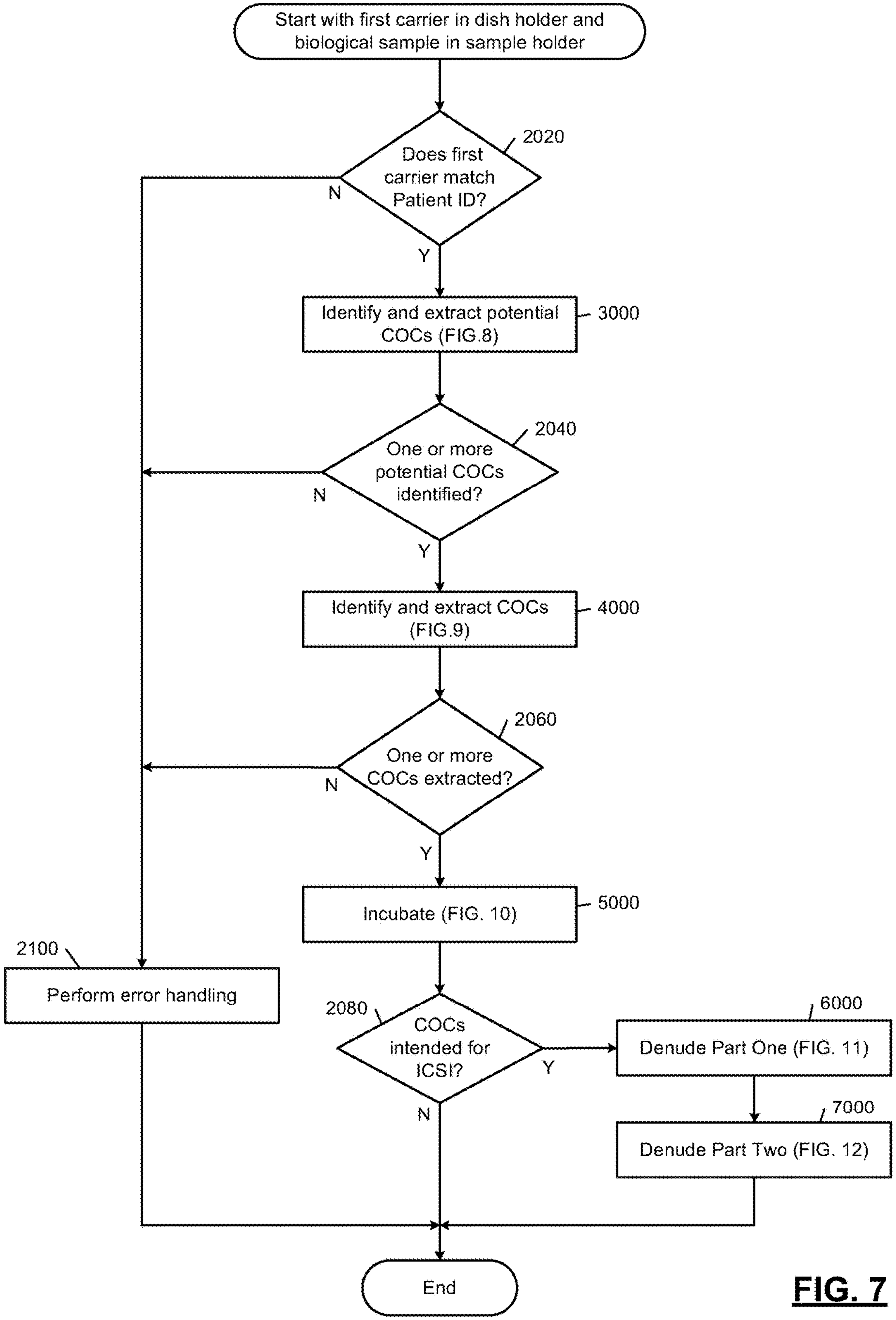
FIG. 7 is an overall flowchart illustrating a method of operation for the platform of FIG. 1 according to the principles of the present disclosure.

Referring to FIG. 7, the method starts with a first carrier, such as the carrier 1000, in the dish holder 340 and one or more biological samples in a sample holder. The first carrier may remain in the dish holder 340 until the platform is ready to perform the method. If the first carrier will remain in the dish holder 340 for an extended period of time (more than a minute or two), then the dish holder 340 may be temperature controlled. The sample holder may also be temperature controlled. The first carrier may be placed in the dish holder 340 by a human operator. In various implementations, the set of robotic arms 400 retrieves the first carrier from an external incubator and transfers the first carrier to the dish holder 340.

At 2020, the carrier identifier (ID) is checked to ensure the method is being performed on the correct biological sample. In various implementations, the carrier ID is compared to patient information to ensure the first carrier matches the patient. If the carrier ID does not match the patient information, control proceeds to 2100 where error handling is performed. Error handling may include replacing the first carrier with a carrier that matches the patient information and returning to 2020 to reinitiate the method. If the carrier ID matches the patient information, control proceeds to 3000.

The external device 900 may image or scan the carrier ID, such as identifier 1060, to determine if the carrier ID matches the patient information and/or if the biological sample is correct. The information gathered from the identifier 1060 may be checked against information about the patient and/or the biological sample stored by the platform 100. For example, the information may be received by the AI/ML system 850, which may determine if the biological sample is correct based on the information. In various implementations, a human operator determines if the biological sample is correct. In various implementations, a human operator may input information about the biological sample into the platform 100.

Figure 8:
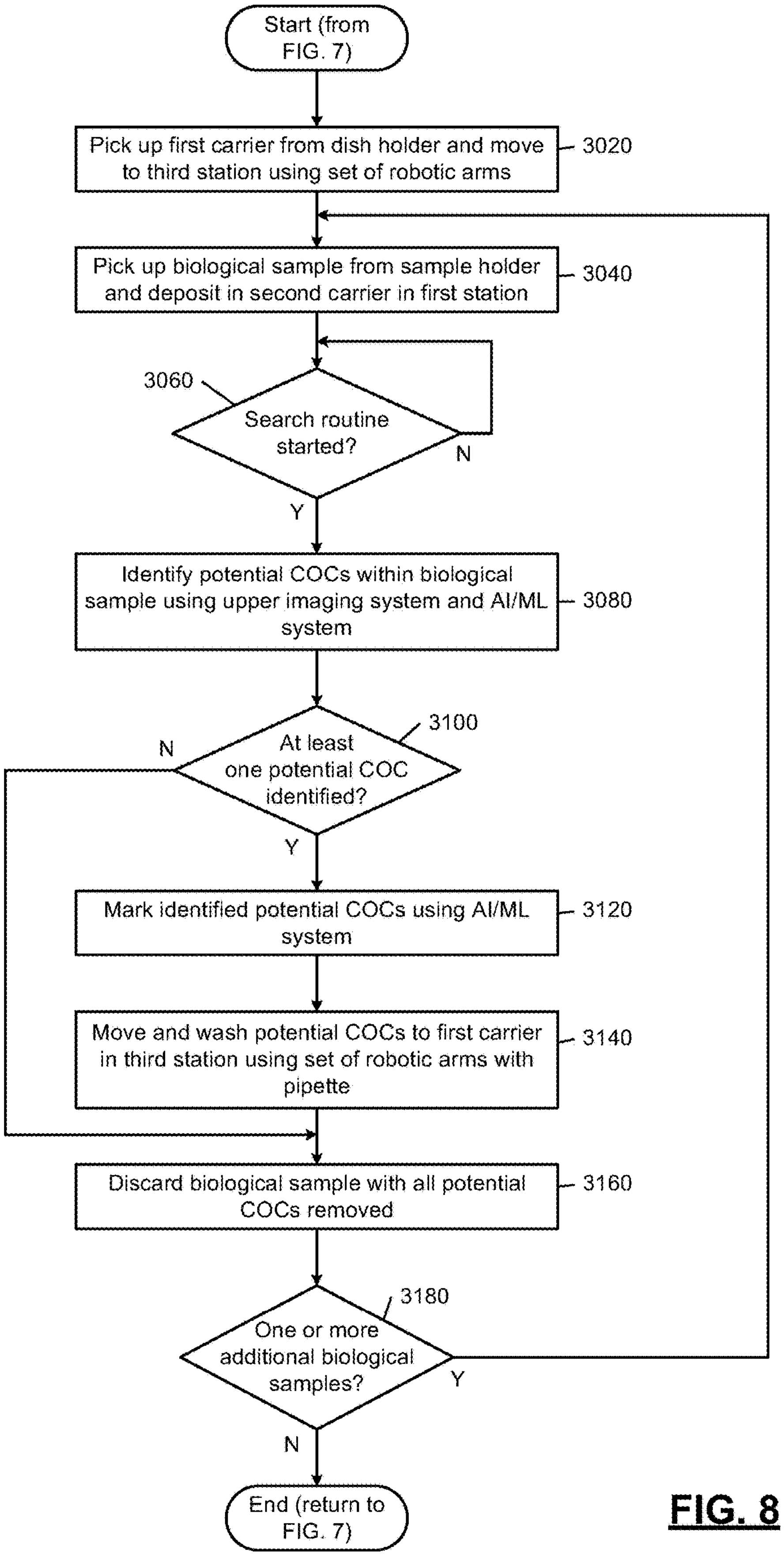
FIG. 8 is a flowchart further illustrating a first portion of the method of FIG. 7.

At 3000, a first sub-routine of identifying and extracting potential COCs is performed. The first sub-routine is illustrated in FIG. 8 and described in more detail below. Upon completion of the first sub-routine, control proceeds to 2040.

At 2040, control checks if at least one potential COC was identified in the first-subroutine. If at least one potential COC was identified, control proceeds to 4000. If no potential COCs were identified, control proceeds to 2100 where error handling is performed. Error handling may include confirming, by a human operator, the absence of any potential COCs and ending the method.

Figure 9:
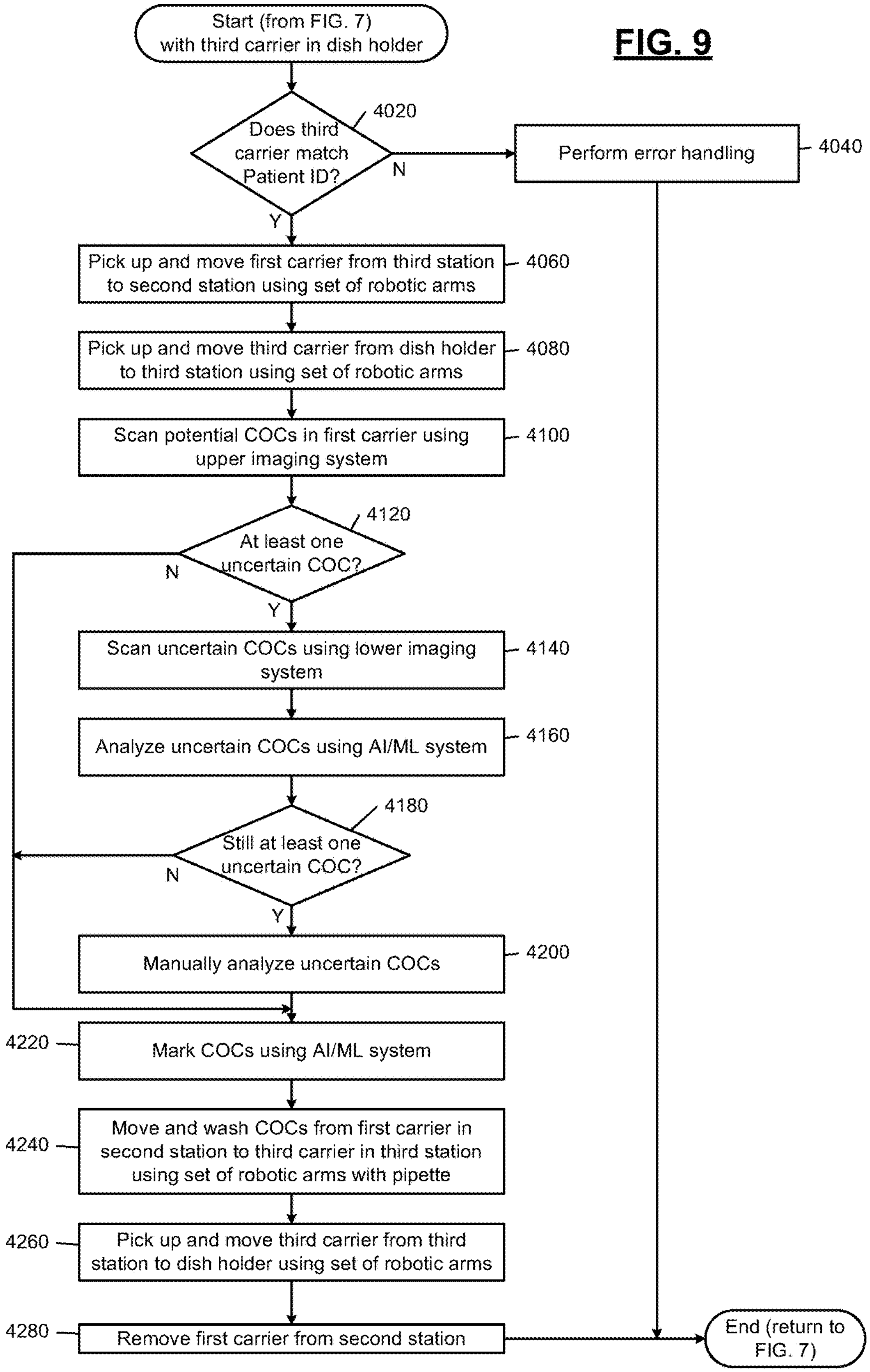
FIG. 9 is a flowchart further illustrating a second portion of the method of FIG. 7.

At 4000, a second sub-routine of identifying and extracting COCs is performed. The second sub-routine is illustrated in FIG. 9 and described in more detail below. Upon completion of the second sub-routine, control proceeds to 2060.

At 2060, control checks if at least one COC was identified and extracted in the second-subroutine. If at least one COC was identified and extracted, control proceeds to 5000. If no COCs were identified and extracted, control proceeds to 2100 where error handling is performed. Error handling may include confirming, by a human operator, the absence of any COCs and ending the method.

Figure 10:
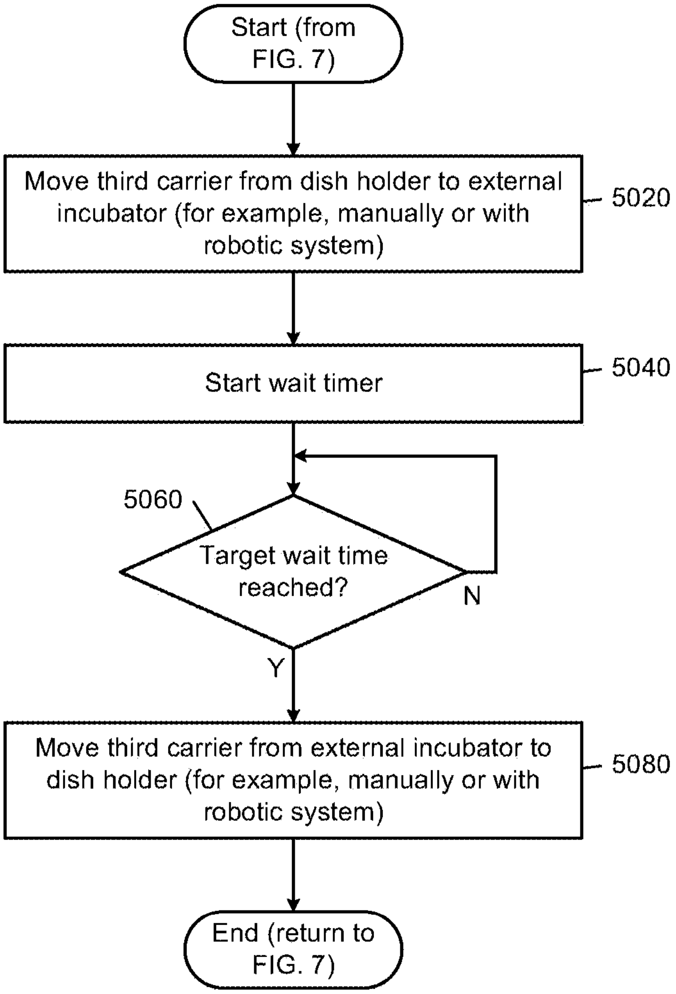
FIG. 10 is a flowchart further illustrating a third portion of the method of FIG. 7.

At 5000, a third sub-routine of incubation is performed. The third sub-routine 5000 is illustrated in FIG. 10 and described in more detail below. Upon completion of the third sub-routine, control proceeds to 2080.

At 2080, control determines if ICSI will performed using the COCs. If ICSI will be performed, control proceeds to 6000. If ICSI will not be performed on the COCs, the method will end.

Figure 11:
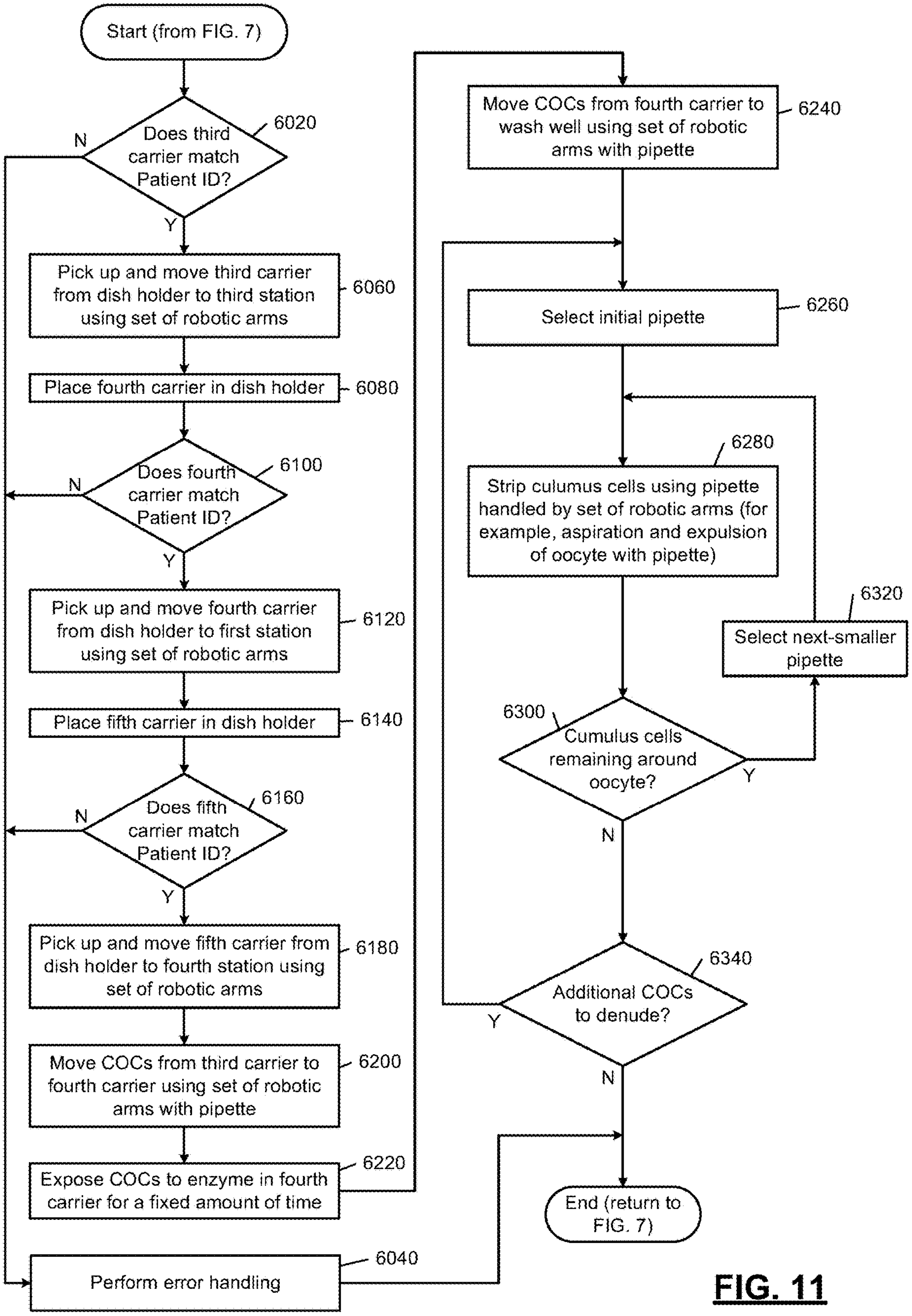
FIG. 11 is a flowchart further illustrating a fourth portion of the method of FIG. 7.

At 6000, a fourth sub-routine of partial denudation is performed. The fourth sub-routine 6000 is illustrated in FIG. 11 and described in more detail below. Upon completion of the fourth sub-routine, control proceeds to 7000.

Figure 12:
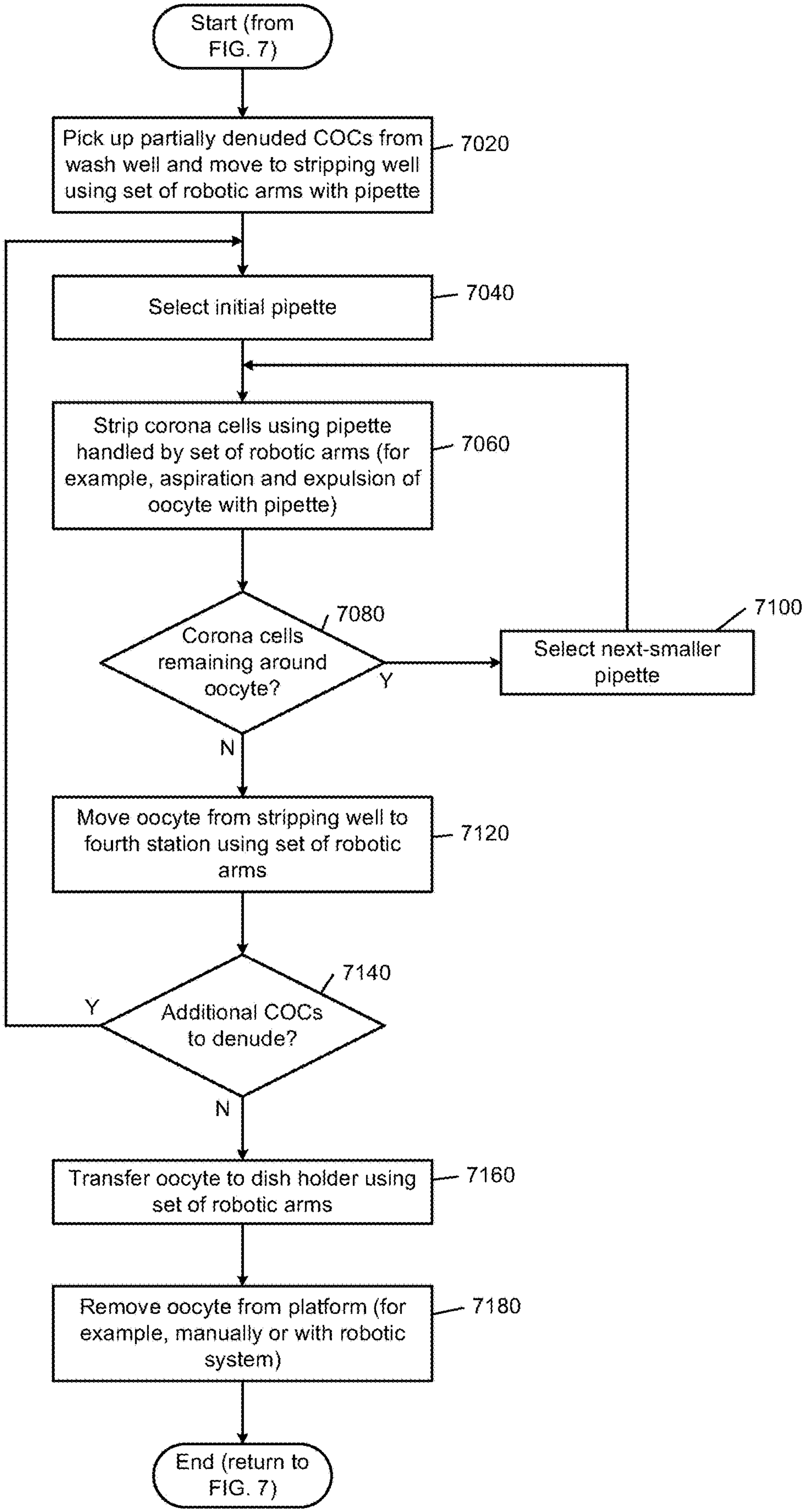
FIG. 12 is a flowchart further illustrating a fifth portion of the method of FIG. 7.

At 7000, a fifth sub-routine of final denudation is performed. The fifth sub-routine 7000 is illustrated in FIG. 12 and described in more detail below. Upon completion of the fifth sub-routine, the method ends.

FIG. 8 illustrates the first sub-routine of identifying and extracting potential COCs. The first sub-routine starts at 3020 where the first carrier is moved from the dish holder 340 to the third station 500-3. For example, the first robotic arm 400-1 may pick up the first carrier with the grabber 490 and move the first carrier to the third station 500-3. This may require the first robotic arm 400-1 to move (translate) along the rail system 410. In various implementations, the first robotic arm 400-1 must pick up and attach the grabber 490 (for example, from a tool storage area) before picking up the first carrier. In various implementations, the first robotic arm 400-1 is controlled by the control unit 800 (for example, the AI/ML system 850). The second robotic arm 400-2 may also be used to move the first carrier from the dish holder 340 to the third station 500-3.

At 3040, the biological sample is retrieved from the sample and deposited in a second carrier that is in the first station 500-1. For example, the first robotic arm 400-1 may pick up the biological sample with the grabber 490 and deposit the biological sample in the second carrier at the first station 500-1. In various implementations, a human operator may pick up the biological sample and deposit the biological sample in the second carrier at the first station 500-1.

At 3060, control checks if a search routine has been started. If the search routine is started, control proceeds to 3080. If the search routine has not been started, control waits and continues to re-check until the search routine is started. The search routine may be a computer program that is executed by the control unit 800 (for example, the AI/ML system 850). In various implementations, the search routine is started automatically. In various implementations, a human operator determines when to start the search routine.

At 3080, potential COCs are identified within the biological sample. In various implementations, the upper imaging system 600 (for example, the set of cameras 620) is used to image the biological sample. The AI/ML system 850 may analyze the images captured by the set of cameras 620 to identify cumulus masses (potential COCs) from within the follicular fluid. In various implementations, the second carrier contains more than one biological sample. For example, the second carrier may contain first and second biological samples stored in separate dishes within the second carrier. In this example, a first camera 620-1 may be used to image the first biological sample and a second camera 620-2 may be used to image the second biological sample. Then, the AI/ML system 850 may analyze the images captured by both the first and second cameras 620-1, 620-2 to identify cumulus masses (potential COCs) in both the first and second biological samples.

At 3100, the presence of at least one potential COC within the biological sample is checked. For example, the AI/ML system 850 may check to determine if at least one potential COC was identified at 3080. If at least one potential COC was identified, control proceeds to 3120. If no potential COCs were identified, control proceeds to 3060, where the biological sample is removed from the platform and a notification is generated indicating the lack of potential COCs. In various implementations, in response to no COCs being identified, the set of robotic arms 400 retrieves the biological sample from the first station 500-1 and transfers it to the dish holder 340 where it may be removed from the platform 100 by a human operator or the set of robotic arms 400.

At 3120, the potential COCs identified in 3080 are marked. Marking the potential COCs may include placing digital markers over the images of the biological sample captured in step 3080. In various implementations, the AI/ML system 850 is trained to automatically place the digital markers. In various implementations, a human operator places the digital markers. The control unit 800 (for example, the AI/ML system 850) may use the digital markers in future steps to locate the potential COCs within the biological sample.

At 3140, the potential COCs are removed from the biological sample, which is in the second carrier in the first station 500-1, and placed in the first carrier, which is in the third station 500-3. In various implementations, the set of robotic arms 400 is used to remove the potential COCs from the biological sample. As discussed above, in instances where there are more than one biological sample in the second carrier, the first robotic arm 400-1 may remove potential COCs from the first biological sample and the second robotic arm 400-2 may remove potential COCs from the second biological sample. In various implementations, both the first and second robotic arms 400-1, 400-2 remove potential COCs from the first and second biological samples. In various implementations, the choice of using the first robotic arm 400-1 or the second robotic arm 400-2 to remove a potential COC depends on the location of the potential COC within the second carrier. For example, if the first robotic arm 400-1 cannot be moved to the necessary angle to remove the potential COC, then the second robotic arm 400-2 may remove the potential COC. In various implementations, the first and/or second robotic arms 400-1, 400-2 manipulates the tool 480 (for example, the pipette) to pick up the potential COCs. In various implementations, picking up the potential COCs with the pipette may remove follicular fluid (and other fluids such as blood) that was surrounding the potential COC, thereby washing the potential COC.

At 3160, once all potential COCs are removed from the biological samples, the biological sample (for example, the second carrier containing the biological sample) is removed from the platform and discarded. For example, the set of robotic arms 400 may retrieve the second carrier from the first station 500-1 and transfer it to the dish holder 340 where it may be removed from the platform 100 by a human operator or the set of robotic arms 400.

At 3180, controls checks if there are more biological samples to be analyzed. If so, the first sub-routine re-starts at step 3040. If there are no more biological samples, the first rub-routine ends.

FIG. 9 illustrates the second sub-routine of identifying and extracting COCs. The second sub-routine starts with a third carrier in the dish holder 340 and the first carrier in the third station 500-3.

At 4020, the carrier identifier (ID) on the third carrier is checked to ensure the third carrier matches the biological sample. In various implementations, the carrier ID is compared to patient information to ensure the third carrier matches the patient. If the carrier ID does not match the patient information, control proceeds to 4040 where error handling is performed. Error handling may include replacing the third carrier with a carrier that matches the patient information and returning to 4020 to reinitiate the second sub-routine. If the carrier ID matches the patient information, control proceeds to 4060.

At 4060, the first carrier, which contains the potential COCs, is moved from the third station 500-3 to the second station 500-2. The first and/or second robotic arms 400-1, 400-2 may grab the first carrier (for example, with the grabber 490) and move the first carrier from the third station 500-3 to the second station 500-2. In moving the first carrier from the third station 500-3 to the second station 500-2, the first and/or second robotic arm 400-1, 400-2 may move (translate) along the rail system 410. In various implementations, movement of the first and/or second robotic arm 400-1, 400-2 is controlled by the control unit 800 (for example, the AI/ML system 850).

At 4080, the third carrier is moved from the dish holder 340 to the third station 500-3. The first and/or second robotic arms 400-1, 400-2 may grab the third carrier (for example, with the grabber 490) and move the third carrier from the dish holder 340 to the third station 500-3.

At 4100, each of the potential COCs is examined, using the upper imaging system 600, to determine if they are a COC (presence of an oocyte) or just a cumulus mass (lack of an oocyte).

At 4120, control checks if there are any uncertain COCs. When the upper imaging system 600 is unable to determine if the potential COC is a COC or just a cumulus mass, the potential COC may be an uncertain COC. If there are no uncertain COCs, control proceeds to 4220. If there is at least one uncertain COC, control proceeds to 4140.

At 4140, the lower imaging system 700 is used to capture images of the uncertain COCs. In various implementations, the OCT imaging system 720 is used to capture images of the uncertain COCs. In various implementations, the microscopy system 740 is used in conjunction with the OCT imaging system 720 to examine the uncertain COCs.

At 4160, the images captured in 4140 may be analyzed by the AI/ML system 850 to determine if an oocyte is present, which indicates that the potential COC is a COC. In various implementations, the OCT imaging system 720 and the AI/ML system 850 is configured to detect the presence or absence of a polar body within the oocyte, which indicates the maturity of the oocyte. In various implementations, the upper imaging system 600 is used in conjunction with the lower imaging system 700 to examine the uncertain COCs.

At 4180, control checks if there are still any uncertain COCs remaining after 4160. If there are no uncertain COCs, control proceeds to 4220. If there is at least one uncertain COC, control proceeds to 4200.

At 4200, any remaining uncertain COCs are analyzed by a human operator who will make the final determination of if a potential COC is a COC or just a cumulus mass. In various implementations, the human operator may review all of the potential COCs to check for misidentification of COCs by the AI/ML system 850.

At 4220, the COCs identified in the previous steps are marked. Marking the COCs may include placing digital markers over the images of the potential COCs captured in the previous steps. In various implementations, the AI/ML system 850 is trained to automatically place the digital markers. In various implementations, a human operator places the digital markers. The control unit 800 (for example, the AI/ML system 850) may use the digital markers in future steps to locate the COCs within the first carrier.

At 4240, the COCs are removed from the first carrier, which is in the second station 500-2, and placed in the third carrier, which is in the third station 500-3. In various implementations, the set of robotic arms 400 is used to remove the COCs from the first carrier. In various implementations, the first and/or second robotic arms 400-1, 400-2 manipulates the tool 480 (for example, the pipette) to pick up the COCs. In various implementations, picking up the COCs with the pipette may remove any fluids that were surrounding the COC, such as a culture medium, thereby washing the COC.

At 4260, the third carrier is moved from the third station 500-3 to the dish holder 340. The first and/or second robotic arms 400-1, 400-2 may grab the third carrier (for example, with the grabber 490) and move the third carrier from the third station 500-3 to the dish holder 340.

At 4280, the first carrier is removed from the second station 500-2, thereby ending the second sub-routine. For example, the first carrier is removed by the set of robotic arms 400 or by a human operator.

FIG. 10 illustrates a third sub-routine of incubating the COCs. In various implementations, the third sub-routine is optional. The third sub-routine starts with the third carrier, which holds all the COCs extracted in the second sub-routine, in the dish holder 340.

At 5020, the third carrier is moved from the dish holder 340 to an external incubator (for example, an incubator that is separate from the platform 100). In various implementations, the set of robotic arms 400 moves the third carrier to the external incubator. In various implementations, a human operator moves the third carrier to the external incubator. The third carrier may be left in the external incubator for a predetermined amount of time.

At 5040, a wait timer is started. For example, the control unit 800 may control a timer used to calculate an amount of time the COCs are in the external incubator.

At 5060, control determines if a target wait time has been reached. If the target wait time has been reached, control proceeds to 5080. If the target wait time has not been reached, control redetermines if the target wait time has been reached. Control does not proceed until the target wait time has been reached. In various implementations, the target wait time is two hours.

At 5080, the third carrier is moved from the external incubator to the dish holder 340, thereby ending the third sub-routine. In various implementations, the set of robotic arms 400 moves the third carrier from the external incubator to the dish holder 340. In various implementations, a human operator moves the third carrier from the external incubator to the dish holder 340.

FIGS. 11 and 12 illustrate fourth and fifth sub-routines, respectively, that collectively denude the COCs either one at a time, or in groups of two or more, or even all at once. The fourth sub-routine starts with the third carrier, which contains the COCs, in the dish holder 340.

At 6020, the carrier ID on the third carrier is checked to ensure the third carrier matches the biological sample. In various implementations, the carrier ID is compared to patient information to ensure the third carrier matches the patient. If the carrier ID does not match the patient information, control proceeds to 6040 where error handling is performed. Error handling may include replacing the third carrier with a carrier that matches the patient information and returning to 6020 to reinitiate the fourth sub-routine. If the carrier ID matches the patient information, control proceeds to 6060.

At 6060, the third carrier is moved from the dish holder 340 to the third station 500-3. In various implementations, the set of robotic arms 400 moves the third carrier to the third station 500-3. In various implementations, a human operator moves the third carrier to the third station 500-3.

At 6080, a fourth carrier is placed in the dish holder 340. In various implementations, the fourth carrier is placed in the dish holder 340 by the set of robotic arms 400. In various implementations, the fourth carrier is placed in the dish holder 340 by a human operator.

At 6100, the carrier ID on the fourth carrier is checked to ensure the fourth carrier matches the patient information. In various implementations, the carrier ID on the fourth carrier is checked to ensure it matches the carrier ID on the third carrier. If the carrier ID does not match the patient information, control proceeds to 6040 where error handling is performed. Error handling may include replacing the fourth carrier with a carrier that matches the patient information and returning to 6080. If the carrier ID matches the patient information, control proceeds to 6120.

At 6120, the fourth carrier is moved from the dish holder 340 to the first station 500-1. In various implementations, the set of robotic arms 400 moves the fourth carrier to the first station 500-1. In various implementations, a human operator moves the fourth carrier to the first station 500-1.

At 6140, a fifth carrier is placed in the dish holder 340. In various implementations, the fifth carrier is placed in the dish holder 340 by the set of robotic arms 400. In various implementations, the fifth carrier is placed in the dish holder 340 by a human operator.

At 6160, the carrier ID on the fifth carrier is checked to ensure the fifth carrier matches the patient information. In various implementations, the carrier ID on the fifth carrier is checked to ensure it matches the carrier ID on the third carrier and/or the fourth carrier. If the carrier ID does not match the patient information, control proceeds to 6040 where error handling is performed. Error handling may include replacing the fifth carrier with a carrier that matches the patient information and returning to 6160. If the carrier ID matches the patient information, control proceeds to 6180.

At 6180, the fifth carrier is moved from the dish holder 340 to the fourth station 500-4. In various implementations, the set of robotic arms 400 moves the fifth carrier to the fourth station 500-4. In various implementations, a human operator moves the fifth carrier to the fourth station 500-4.

At 6200, the COCs are moved from the third carrier, which is in the third station 500-3, to the fourth carrier, which is in the first station 500-1. In various implementations, the set of robotic arms 400 is used to remove the COCs from the third carrier. In various implementations, the first and/or second robotic arms 400-1, 400-2 manipulates the tool 480 (for example, the pipette) to pick up the COCs.

At 6220, the COCs are exposed to an enzyme, such as hyaluronidase. In various implementations, the culture container(s) in the fourth carrier includes multiple wells and the COCs are placed in a first well of the multiple wells. In various implementations, the first well contains the enzyme, such as hyaluronidase. The enzyme may disperse the cumulus mass from the oocyte. In various implementations, the first and/or second robotic arm 400-1, 400-2 manipulates the tool 480 (for example, the pipette) to expel the enzyme into the carrier 1000 and/or culture container 1100 containing the COCs. In various implementations, expulsion of the enzyme is controlled by the control unit 800 (for example, the AI/MVL system 850). In various implementations, the enzyme removes most, but not all of the cumulus cells from the oocyte. For example, the enzyme may not remove the corona cells from the oocyte.

At 6240, the COCs are moved from the first well to a second well in the fourth carrier. In various implementations, the set of robotic arms 400 is used to move the COCs to the second well. In various implementations, the first and/or second robotic arms 400-1, 400-2 manipulates the tool 480 (for example, the pipette) to move the COCs.

At 6260, an initial pipette, having a first size (diameter), is selected. In various implementations, the AI/ML system 850 selects the initial pipette. In various implementations, a human operator selects the initial pipette.

At 6280, any cumulus cells that remain after exposure to the enzyme are stripped from the oocyte. In various implementations, the cumulus cells are removed by repeatedly aspirating the oocyte into the initial pipette and expelling the oocyte from the initial pipette, which is manipulated by the first and/or second robotic arm 400-1, 400-2.

At 6300, control checks if any cumulus cells are remaining around the oocyte. In various implementations, the AI/ML system 850 is used to determine if any cumulus cells are remaining around the oocyte. If there are no cumulus cells remaining, control proceeds to 6340. If any cumulus cells are still present, control proceeds to 6320.

At 6320, another pipette is selected that has a smaller size (diameter) than the initial pipette. In various implementations, the AI/ML system 850 selects the next pipette. In various implementations, a human operator selects the next pipette. Control proceeds back to 6280. Steps 6280, 6300, and 6320 are repeated until no cumulus cells remain around the oocyte. At this stage, the COCs are partially denuded.

At 6340, control determines if there are additional COCs to denude. If there are additional COCs to denude, control proceeds to 6260 and steps 6260, 6280, 6300, and 6320 are performed on the additional COCs. If there are no additional COCs to denude, the fourth sub-routine ends.

The fifth sub-routine begins at 7020, where the partially denuded COCs are moved from the second well to a third well of the fourth carrier. In various implementations, the set of robotic arms 400 is used to move the partially denuded COCs to the third well. In various implementations, the first and/or second robotic arms 400-1, 400-2 manipulates the tool 480 (for example, the pipette) to move the partially denuded COCs.

At 7040, an initial pipette, having a second size (diameter), is selected. In various implementations, the AI/ML system 850 selects the initial pipette. In various implementations, a human operator selects the initial pipette.

At 7060, corona cells are stripped from the oocyte. In various implementations, the corona cells are removed by repeatedly aspirating the oocyte into the initial pipette and expelling the oocyte from the initial pipette, which is manipulated by the first and/or second robotic arm 400-1, 400-2.

At 7080, control checks if any corona cells are remaining around the oocyte. In various implementations, the AI/ML system 850 is used to determine if any corona cells are remaining around the oocyte. If there are no corona cells remaining, control proceeds to 7120. If any corona cells are still present, control proceeds to 7100.

At 7100, another pipette is selected that has a smaller size (diameter) than the initial pipette. In various implementations, the AI/ML system 850 selects the next pipette. In various implementations, a human operator selects the next pipette. Control proceeds back to 7060. Steps 7060, 7080, and 7100 are repeated until no corona cells remain around the oocyte. At this stage, the COC is completely denuded and only the oocyte remains.

At 7120, the oocyte is moved from the third well to the fifth carrier, which is in the fourth station 500-4. In various implementations, the set of robotic arms 400 is used to move the oocyte to the fifth carrier. In various implementations, the first and/or second robotic arms 400-1, 400-2 manipulates the tool 480 (for example, the pipette) to move the oocyte.

At 7140, control determines if there are additional partially denuded COCs to denude. If there are additional partially denuded COCs to denude, control proceeds to 7040 and steps 7040, 7060, 7080, and 7100 are performed on the additional partially denuded COCs. If there are no additional COCs to denude, control proceeds to 7160.

At 7160, the fifth carrier, which contains the oocytes, is moved from the fourth station 500-4 to the dish holder 340. In various implementations, the set of robotic arms 400 is used to move the oocytes to the dish holder 340.

At 7180, the fifth carrier is removed from the platform 100 and the method ends. In various implementations, the set of robotic arms 400 is used to remove the fifth carrier from the platform 100. In various implementations, a human operator removes the fifth carrier from the platform 100.

Additional Details

An IVF/ICSI platform, as described herein, can include automation of traditionally manual laboratory activities between robotic systems used in assisted reproduction (inter-robotic), and automation of traditionally manual laboratory activities preparing for specific robotic procedures (intra-robotic), including, but not limited to, 1) diagnostic semen analysis, such as computer assisted sperm analysis; 2) continuous embryo culture, including employing robotic handling of dishes combined with time-lapse microscopy technology with manual or automated embryo development annotation; 3) cryopreservation and cryo-storage automation, including automated cryo-storage processes in clinical IVF allowing for precise sample location monitoring and continuous environmental status monitoring; and 4) micromanipulator usage, including robotic systems for single-cell surgery, offering fine and coarse control movement modulators, some with digital control for precise tool manipulation.

The IVF/ICSI platform improves upon existing methods and systems, in part, by automating intra- or inter-patient pipette and tool setup, dish preparation, or tracking of disposables and biological materials by integrating traditional IVF laboratory processes into a conveyor-type robotic line (linear or otherwise), including, but not limited to, automated semen analysis, sperm preparation, petri dish preparation, egg retrieval, oocyte vitrification, egg denudation, time-lapse incubation, ICSI, embryo selection, embryo vitrification preparation, robotic plunging into liquid nitrogen, embryo transfer, cryo-storage, and other IVF systems, methods, processes and procedures. The conveyance system used by the IVF/ICSI platform to transport tools, equipment, biological material, human samples, refuse, and other facilities, components, material and/or objects used by the IVF/ICSI platform to transport such from a first location or position to a second location or position can include, but is not limited to, a conveyor belt, a rail-based conveyance, a sequential robotic movement, a roller conveyor, a chain conveyor, a gravity conveyer, an overhead conveyor, a flexible conveyor, a pneumatic conveyor, an auger conveyor, a screw conveyor, a vacuum conveyor, a vibrating conveyor, or some other type of conveyance.

The IVF/ICSI platform can include an inter-robotic IVF system protocol that includes processes for coordinating robotic elements across distinct IVF procedures, specifically addressing the interconnection of robotic stages within the IVF/ICSI platform 10, thereby reducing human intervention, minimizing costs, enhancing operational speed, and ensuring the secure and efficient transfer of samples between different robotic modules of the IVF/ICSI platform 10. The IVF/ICSI platform can include a comprehensive documentation system to record, monitor and report on the performance of the inter-robotic IVF system, including parameters related to sample transfer, system efficiency, and any incidents for analysis and continuous improvement. The IVF/ICSI platform can be adaptable to changes in IVF laboratory setup and scalable to accommodate future expansions or modifications.

The IVF/ICSI platform can include intra-robotic systems and procedures for configuring an intra-robotic IVF system, encompassing microscopy and non-microscopy robotic elements involved in a specific procedure. Such intra-robotic systems and procedures can standardize setup for each patient, ensuring the incorporation of both disposable and non-disposable components into each robotic platform. In an example intra-robotic IVF system procedure, the availability of necessary components for a specific patient procedure can be verified and the procedure can ensure that both disposable and non-disposable items are in stock and within the designated sterile environment. Sterile and non-sterile components can be positioned on the robotic platform according to a standardized layout, in part to allow flexibility in the positioning of individual components, accommodating variations in patient or procedural requirements, and to facilitate adjustments to the setup. Sterility protocols can be implemented by the system when handling and placing sterile components on the robotic platform, which can also regularly assess and maintain the integrity of sterile barriers throughout the procedure. The system can document the configuration of the intra-robotic IVF system for each patient procedure and include details on the positioning of disposable and non-disposable components, allowing for comprehensive records and potential future optimizations.

The inter- and intra-robotic systems of the IVF/ICSI platform can include a comprehensive software system for the coordination and management of IVF processes and integrated laboratory robots. This system can track samples, monitor environmental conditions, monitor and instruct robotic systems, control the timing of all procedures, detect faults or inefficiencies, and report to electronic medical records (EMR) to allow for patient scheduling and patient instructions. The software system can monitor the safety aspects of the robotic system, including maintenance and service requirements.

An egg preparation module can include a robotic system, having egg retrieval and preparation components, systems, and processes, that is used for egg retrieval and preparation. The egg preparation module can include AI for automated detection, identification, and classification, for automated measurement and testing, and for optimization, prediction, and/or selection/ranking. The egg preparation module can include AI for semi-autonomous, supervised, or autonomous robotics, as well as for system configuration and control. The egg preparation module can also include fully autonomous AI. The egg preparation module can additionally include a variety of other components, including, but not limited to optical, image and machine vision components, systems, and processes; robotic handling systems and processes; sensor components, systems, and processes; specimen management components, systems, and processes; enzymatic oocyte denudation processes, systems and components; and advanced microscopy systems and components.

Egg Retrieval

In embodiments of the present invention, the IVF/ICSI platform, as described herein, may include an egg preparation module that is fully automated, uses robotics for the handling and movement of materials, including biological specimens, and is connected to a network infrastructure, as described herein, for remotely controlling the activities of the egg preparation module as one component of the fully automated and robotic IVF/ICSI platform.

In embodiments, in a clinical setting follicle stimulating hormone (FSH) may be administered to a patient to stimulate the ovary/ies to grow multiple follicles, and an ultrasound-guided transvaginal procedure used, entailing aspiration of the growing follicles, while the patient is under sedation. The follicles are punctured using a thin needle, and the fluid within is aspirated into tubes. A mature antral follicle at ovulation may measure ~25 mm in diameter and contains ~50 million granulosa cells and ~7 ml of follicular fluid. Follicular fluid is often opaque yellow in color and contains hormones (e.g., estrogen, progesterone, androgens, etc.), growth factors, cytokines, metabolites (e.g., glucose, pyruvate, lactate, etc.), ions (e.g., sodium, potassium, calcium, etc.), and proteins (e.g., albumin, transferrin, etc.) among other factors. Cellular components of the follicular fluid may include granulosa cells: As an (antral) follicle develops, distinct classes of functionally different granulosa cells are generated depending on the position of the granulosa cells relative to the oocyte. The cells closest to the oocyte are cumulus granulosa cells, while mural granulosa cells are further away from the oocyte and line the follicle wall. In response to ovulation trigger, cumulus cells secrete an extracellular matrix primarily made up of hyaluronan (therefore hyaluronidase-sensitive) that causes expansion of the cumulus cells in a process called mucification. Mucified or expanded cumulus masses appear translucent and distinct from mural granulosa cells, which maintain their sheet-like tight-knit morphology with a darker appearance and thus can be visually distinguished from cumulus even with a naked eye.

In embodiments, biologic material obtained from a patient during egg retrieval may include an oocyte-cumulus-corona-complex (OCCC) or cumulus-oocyte-complex (COC): Corona radiata cells are the layer of cells that directly contact the zona pellucida, the acellular glycoprotein moiety or "shell" surrounding the oocyte via cytoplasmic projections. During cumulus expansion, the corona radiata cells may be separated from the zona pellucida but they are still recognizable as a distinct layer of cells surrounding the oocyte. They do not undergo mucification and usually appear darker than the cumulus cells, facilitating visual identification of oocytes. Hyperstimulated ovaries have increased vascularity and the follicles are more prone to bleeding when punctured by the retrieval needle. This can lead to mixing of blood with follicular fluid.

In embodiments, oocytes isolated from follicular fluid may be at different stages of nuclear maturation, for example, fully mature (at metaphase II or MII of meiosis with a first polar body present), intermediately mature (at metaphase I of meiosis; no polar body) and immature (at prophase I of meiosis, containing a large nucleus called a germinal vesicle or GV). Depending on the level of nuclear maturity, the cumulus masses can appear with different morphology: expanded and translucent in MII oocytes; somewhat darker and more tightly organized in MI oocytes; and very dark, tight, and small in GV oocytes. Nuclear maturity may be estimated based on the appearance of the cumulus and corona cells.

In embodiments, the IVF/ICSI platform may autonomously and robotically perform oocyte search and isolation, replacing the traditional egg retrieval procedure performed by a human operator. In the traditional egg retrieval procedure performed by a human operator, the processes listed in Table 1, below, are generally followed.

TABLE 2

| Action | Human operator role |
|---|---|
| Patient identification | Document verification; patient contact; Human judgment |
| Planning case preparation | Human judgment |
| Preparation of dishes for oocyte retrieval procedure (Wash dishes, culture dishes) | Pipetting, transport |
| Preparation of tubes for follicle flushing | Pipetting |
| Verification of patient identity on dishes | Witnessing; Human judgment |

TABLE 2-continued

| Action | Human operator role |
|---|---|
| Receiving tubes with follicular aspirates from the operating theatre | Manual handling of tubes |
| Decanting tube contents in one or more dishes | Manual handling of tubes |
| Scanning dishes for cumulus complexes | Macroscopic examination |
| Identifying cumulus complexes containing oocytes | Microscopic examination (LP) |
| Picking up the OCCCs ad placing them in a wash dish | Pipetting; (PASTEUR) changing dishes |
| Repeating the process and counting number of OCCCs | Manual handling of tubes/dishes; pipetting (PASTEUR) Changing dishes |
| Dissecting blood- stained cumulus masses | Macro-manual; microscopic observation |
| Placing OCCCs in culture dish/es | Pipetting; change of dish |
| Placing dish/es in designated incubator | Transport and knowledge of correct location |
| Data entry on paper/EMR | Macro-manual |

In embodiments, aspirates of follicular fluid may be searched under a stereo microscope by an embryologist to identify and isolate COCs. The cumulus investment of eggs may be dissected using hypodermic needles to remove blood clots or unhealthy-appearing cells or to simply reduce its size before incubation.

In embodiments, pipetting in the context of egg retrieval may entail aspiration and expelling and container-to-container transfer of individual or multiple COCs. Pipetting is fundamental to IVF laboratory techniques and may be carried out in a sterile fashion, without creating air bubbles that could be disruptive, lead to loss of cells, or create potentially infectious aerosols. Different types of pipettes may be used by the automated, robotic pipetting systems and methods of the IVF/ICSI platform, as described herein, during egg retrieval procedures, including but not limited to Pasteur pipettes, Eppendorf pipettes, capillary tube tips, or some other type of pipette. Pasteur pipettes are made of borosilicate glass, usually in two lengths (short or 5.75 inches and long or 9 inches) and may be used in conjunction with rubber pipette bulbs, to transfer smaller volumes of fluids with or without cells. These pipettes can be "pulled" over a flame to create very narrow bores for handling eggs and embryos. Eppendorf pipettes are instruments equipped with a piston and a spring-loaded tip cone, single channel and adjustable volumes (1-1000 μL units with specific ranges), used in conjunction with Eppendorf tips, to aspirate and dispense precise (usually low) volumes. capillary tube tips refer to pipette tips used in conjunction with capillary tube pipettors: Tips are made from flexible medical grade plastic to prevent scratching of plastic Petri dishes. The tips are manufactured in different inner diameters, ranging from 75 μm to 600 μm, with the most commonly used sizes being 155-200 μm for denudation of eggs and handling eggs and embryos, and 300 μm for handling blastocysts.

The automated IVF/ICSI platform may use robotics for isolation, handling and movement of eggs with their investments (COCs) from follicular fluid. The follicular aspirates may be decanted in a dish and placed on a motorized stage of an inverted microscope. The dish may be automatically scanned in a predetermined pattern, using computer vision, in combination with AI/ML and/or computer vision and optics, as described herein, in order to identify the COC. Once identified, the COC may be automatically retrieved with a pipette, washed, and transferred to a new dish containing fresh handling medium.

In embodiments, an example, simplified sequence for oocyte isolation is presented below, each element of which may be performed autonomously and robotically by the IVF/ICSI platform, as described herein:

A "wash" dish (e.g., 1×35 mm) with handling medium and an oil overlay (to prevent evaporation) may be received by the IVF/ICSI platform and placed on a stage of an inverted microscope, or some other type of microscope, fitted with a "dish holder" (e.g., a rectangular piece with cut-outs to fit one 60 mm and 2×35 mm culture dishes).

The IVF/ICSI platform may begin a sequence with movement of the stage as computer vision is used to scan the dish, for example, in a pre-determined zig-zag pattern from top to bottom.

AI/ML may identify cumulus masses containing eggs. Each aspirate may contain zero to multiple eggs. This is partly dependent on the method of aspiration used by the surgeon and the size of the follicles being aspirated. Individual follicles may be aspirated into each tube or multiple follicles may be aspirated at the same time into one tube. The ratio of eggs to tubes may be other than 1:1; there may be more tubes of aspirates and flushing medium than eggs; or multiple eggs in one tube. The robotics of the IVF/ICSI platform, as described herein, may be able to distinguish among the different contents and identify the eggs. In embodiments, processes 3 and 4 may or may not occur in parallel. In an example, while the dish is being scanned, computer vision, optics and/or AI/ML may be used to search for and identify COCs, or the process might also stop the scanning at a given position to interact with the computer vision, optics and/or AI/ML, and/or the IVF/ICSI platform might obtain images of the follicular fluid in the scanning process and after finalizing the scan, query the computer vision, optics and/or AI/ML to determine if there are any COCs present.

Once identified, a pipette held in a microtool holder may be lowered into the follicular fluid dish and placed immediately adjacent to the cumulus mass. In an embodiment, the pipette tip may be lowered at a distance from the COC, and once inside the liquid it may approach the COC, and then begin aspiration.

Negative pressure may then be applied and the cumulus mass along with some fluid may be aspirated into the pipette.

The amount of fluid may be precisely controlled based on the outer physical limits of the mass. Aspiration may stop once the full mass is inside the pipette. Then the pipette may be lifted out of the dish and remain stationary.

The stage may then move toward the first dish with handling medium.

Once in place, the pipette may be lowered into the wash dish, positive pressure may be applied, and the cumulus mass/follicular fluid may be expelled into the medium. The volume may be precisely controlled so that positive pressure stops once the entire mass exits the pipette.

The pipette may then be lifted out of the dish and remain stationary.

In embodiments, the egg preparation module may receive a follicular fluid specimen and automatically place the specimen for viewing with a microscope, computer or machine vision, or some other imaging device, in order to perform cumulus oocyte complex (COC) identification, discovery, analysis and evaluation. In an example embodiment, the specimen may be viewed within the egg preparation module using an inverted microscope, a digital microscope, or some other type of microscope. In embodiments, the inverted microscope may include components and adapted robotics to be used as part of an automated ICSI procedure, as described herein, and may include digital microscopes both under and over of the plates, dishes or other type of vessels containing the samples. The follicular fluid specimen may be automatically scanned using computer vision, machine vision and the like, in combination with AI/ML in order to perform the COC identification. This imaging in combination with AI/ML may allow differentiating of cell types, such as that of blood cells from COCs.

In embodiments, during the COC identification stage, the egg preparation module may autonomously and robotically place the dish, receptacle or vessel in which the follicular fluid specimen is located on a stage, plate or other surface that is motorized to provide movement to the dish, receptacle or vessel in which the follicular fluid specimen is located. In various implementations, dish holders may be used by the egg preparation module for holding a specimen dish, receptacle or vessel. As the imaging and AI/ML procedures are carried out on the follicular fluid specimen, the egg preparation module may automatically adjust the positioning of the dish, receptacle or vessel in which the follicular fluid specimen is located in order to optimize, for example, the angle, height, or portion of the specimen as it is imaged. The stage, plate or other surface may move in any axis of movement and may rotate along any axis or plane of operation.

In embodiments, imaging of the specimen within the egg preparation module may be made independently of the microscope or through the microscope. For example, one set of imaging equipment may be used to evaluate and analyze the positioning of certain equipment independent of the microscope, such as the position of a dish, receptacle or vessel being used within the egg preparation module. In embodiments, imaging may be made through the optics of the microscope as well, for example, by fitting a camera or plurality of cameras to the microscope viewing apparatus, such as binocular scopes. In embodiments, during imaging, the egg preparation module may automatically adjust the frequency, intensity, angle, distance or some other factor of artificial lighting that is used to image the specimen. The adjustment of the frequency, intensity, angle, distance or some other factor of artificial lighting that is used to image the specimen may be based at least in part on the AI/ML processes used to evaluate the imagery obtained of the follicular fluid sample by the egg preparation module.

In embodiments, once at least one COC is identified, for example by using the inverted microscope in combination with imaging and AI/ML, as described herein, a pipette may vertically descend into the follicular fluid specimen and extract at least one COC and transfer the selected COC to a second dish, receptacle or vessel within the egg preparation module that contains culture media. The dish, receptacle or vessel into which the COC(s) are placed may reside on or in the vicinity of a plate that is capable of temperature control, such as providing the dish, receptacle or vessel a constant 37-degree Celsius (or some other target temperature) environment during the performance of the COC washing and preparation. During this process, if more than one COC is identified within the specimen, the egg preparation module may further separate the COCs into additional dishes, receptacles or vessels to provide for a single COC per each divided sample, or some other targeted number of COCs per divided sample.

In embodiments, during the COC identification and separation stage, the egg preparation module may automatically apply compounds to the specimen in order to facilitate COC separation and extraction. In an example, if the imaging and AI/ML procedures of the egg preparation module detect the presence or probability of blood or blood clotting in the follicular fluid sample, the egg preparation module may robotically select an amount of heparin, or other clot prevention therapeutic, and add the heparin to the follicular fluid sample to facilitate COC extraction. The type of clot prevention therapeutic, the amount of clot prevention therapeutic, the timing of the addition of the clot prevention therapeutic to the follicular fluid sample, and other factors, may be determined at least in part automatically using the imaging and AI/ML processes of the IVF/ICSI platform, as described herein.

Washing

In embodiments, once the COCs have been autonomously and robotically placed in the dish, receptacle or vessel containing the culture media, the COCs may then be moved to a new dish, receptacle or vessel where the egg preparation module performs an autonomous and robotic series of washes of the COCs. Following the washing of the COCs, the dish, receptacle or other vessel in which the COCs are contained may be automatically transferred to an incubator.

In embodiments, after a period of culture of COCs, the egg preparation module may autonomously and robotically initiate an oocyte denudation process.

In embodiments, automation, as used herein, includes robotics and AI/ML-assisted processes so that processes in the egg denudation procedures that ordinarily require a human operator may be performed by the intelligent robotic system of the IVF/ICSI platform. Table 2 outlines such processes involved in traditional oocyte denudation:

TABLE 3

| Action |
|---|
| Enzyme and wash dish preparation |
| Determination of timing of denudation in relation to ovulation trigger |
| Transfer of dish with oocytes from the incubator to the laminar flow hood |
| Verification of patient identity on all dishes |
| Transfer of eggs in groups of 1-5 (based on total number of eggs) from incubation dish to the enzyme dish/well |
| Gentle pick up and expelling of OCCCs in and out of the pipette |
| Allowing the enzyme to dissociate/disperse cumulus cells |
| Moving the oocyte-corona complexes with loosely arranged or fully dissociated cumulus cells out of the enzyme drop/well & into a clean medium drop/well |
| Removing corona cells mechanically using sequentially smaller capillary tube tips (200 to 155 um) |
| Moving the corona-free eggs to a new well/drop with fresh medium & repeat |
| Assessing nuclear maturity of the eggs |
| Separate MII from MI and GV oocytes in different wells/drops |
| Use MII eggs for ICSI or MII and MI eggs for vitrification |
| Placing dish/es in designated incubator |
| Data entry/EMR |

As an (antral) follicle develops, distinct classes of functionally different granulosa cells are generated depending on the position of the granulosa cells relative to the oocyte. The cells closest to the oocyte are called cumulus cells (or cumulus oophorous). Immediately surrounding the oocyte are corona radiata cells which directly contact the zona pellucida via cytoplasmic projections. During cumulus expansion (following ovulation trigger), the corona radiata cells are separated from the zona pellucida (the projections are mostly withdrawn) but they are still recognizable as a distinct layer of cells surrounding the oocyte. They do not undergo mucification and usually appear darker than the cumulus cells, facilitating visual identification of oocytes.

In embodiments, oocytes isolated from follicular fluid may be at different stages of nuclear maturation: fully mature (at metaphase II or MII of meiosis with a first polar body present), intermediately mature (at metaphase I of meiosis; no polar body) and immature (at prophase I of meiosis, containing a large nucleus called a germinal vesicle or GV). Depending on the level of nuclear maturity, the cumulus masses may appear with different morphology: expanded and translucent in MII oocytes; somewhat darker and more tightly organized in MI oocytes; and very dark, tight, and small in GV oocytes. While nuclear maturity may be reasonably estimated based on the appearance of the cumulus and corona cells, oocyte development potential cannot be assessed in this way.

In embodiments, prior to injecting oocytes with sperm, the cumulus-corona complex may be removed so the egg can be visualized and micromanipulated. Complete removal of cumulus and corona cells is called denudation. This is accomplished enzymatically and mechanically. The enzyme hyaluronidase may be used to dissociate cumulus cells. This is possible because the expanded cumulus is a hyaluronan (HA)-rich extracellular matrix. Corona cells, on the other hand, may be removed mechanically since they do not undergo mucification. Mechanical removal may be accomplished by repeated aspiration/expelling using small inner diameter pipettes, for example 155-200 uM capillary tube tips or hand-drawn Pasteur pipettes.

In embodiments, pipetting in the context of denudation may entail aspiration and expelling and container-to-container transfer of individual or multiple OCCCs and oocytes. Pipetting is fundamental to all IVF laboratory techniques and may be carried out in a sterile fashion, without creating air bubbles that could be disruptive, lead to loss of cells, or create potentially infectious aerosols. Different types of pipettes may be used during denudation procedures, including but not limited to: Pasteur pipettes: Made of borosilicate glass, for example in two lengths (short or 5.75 inches and long or 9 inches) and used in conjunction with rubber pipette bulbs, to transfer smaller volumes of fluids with or without cells. These pipettes can be "pulled" over a flame to create very narrow bores for handling eggs and embryos. Eppendorf pipettes: Instruments equipped with a piston and a spring-loaded tip cone, single channel and adjustable volumes (1-1000 μL units with specific ranges), used in conjunction with Eppendorf tips, to aspirate and dispense precise (usually low) volumes. Capillary Tube Tips: Pipette tips used in conjunction with "Stripper" or "EZ-grip" pipettors: Tips are made from flexible medical grade plastic to prevent scratching of plastic Petri dishes. The tips may be manufactured in different inner diameters, ranging from 75 μm to 600 μm, with the commonly used sizes being 155-200 μm for denudation of eggs and handling eggs and embryos, and 300 μm for handling blastocysts.

In embodiments, an example hardware set up for denudation related processes may include, but is not limited to, the following equipment that may be integrated within the IVF/ICSI platform, as described herein:

Inverted Microscope (Olympus IX81)
Stage movement controller (Prior H117P2IX)
Microscope Dino-Lite Edge (5mp Series)
ArduCam (IMX477 12MP)
Stage Heating & Controller (TokaiHit)
Micromanipulators (Eppendorf; TransferMan 4r)
Range of 12,500 μm for each axis
Max speed of 10,000 μm per second
Microinjector (Narishige IM-21)
10 μL per turn
400 μL total
W127-147×D56×H78 mm
Microtool Holder (HI-7)
W140×D8×H78 mm
2 Stepper motors (5PCS Nema 17)
LCPlanFI 20× Olympus
UPlanFLN 4× Olympus
Motor controller BTT SKR Mini E3 v3.0

In embodiments, the automated oocyte, AI/ML-assisted identification and isolation system of the IVF/ICSI platform may minimize and/or eliminate the need for a skilled embryologist for denudation of oocytes in preparation for ICSI or cryopreservation.

In embodiments, during the denudation process, a stereomicroscope, an inverted microscope, or some other microscope type, may be used to image the specimen that is held within a dish, including a flat dish and/or a dish having a plurality of wells, for example four or more wells within the dish. A first well may contain an enzyme that allows for the removal of the cumulus cells from the oocyte. A pipette may be used to, in repetition, draw the oocyte from the well into the pipette and then expel the oocyte from the pipette allowing for removal of cumulus and corona cells via enzymatic action and also from the mechanical force of the pipette drawing and expelling the oocyte in an automated manner using robotic processing. In an example, the egg preparation module may also facilitate denudation by automatically using the pipette, or other device, to perturb the fluid in which the COCs are held. As the process of denudation progresses, the imaging and AI/ML processes, as described herein, may be used to periodically, or continuously, evaluate and analyze the extent of the corona cell removal and indicate once a targeted end point is reached or surpassed, at which time the corona cell removal process may be ended. Because prolonged exposure to enzymes has the potential to damage the oocyte, usage of the imaging and AI/ML processes may facilitate reducing the time of exposure by allowing for the rapid identification of completed preparation and reduce stress to the egg. In embodiments, the egg preparation module may use an adapter to use single cell holders with standard needle holders.

In embodiments, once the corona cells have been adequately removed from the COC, the egg preparation module may autonomously and robotically begin a washing process, using a number of wells within a dish, receptacle or vessel in which to perform the washing. Following washing the egg preparation module may automatically assess the maturity of an egg using imaging and AI/ML processes, as described herein. In one aspect, the imaging and AI/ML processes may evaluate the morphology of the egg to assist in determining the maturity, for example, determining if the egg has a polar body or not. If the imaging and AI/ML processes determine that there is a polar body present, the egg may be considered mature by the IVF/ICSI platform and considered as eligible to proceed to the insemination module of the IVF/ICSI platform, as described herein. If the imaging and AI/ML processes determine that there is no polar body present, the egg may be considered immature by the IVF/ICSI platform and automatically returned for further incubation, and a subsequent round of maturity assessment performed by the imaging and AI/ML processes once a further incubation cycle is completed. In embodiments, continuous monitoring using time-lapse may be used for assessment.

In embodiments, the egg preparation module and incubation module may be operatively coupled components of the intelligent, automated system of the IVF/ICSI platform. The egg preparation module may be responsible for the retrieval, identification, classification, measurement, testing, optimization, prediction, selection/ranking, and handling of eggs, employing AI/ML processes, robotic handling systems, and advanced microscopy systems to perform these tasks, as described herein. In an example, once the egg preparation module has completed the tasks of identifying and retrieving an egg, the egg may be automatically and robotically transferred to the incubation module. The incubation module may include components and systems for incubation, sensor components for monitoring the conditions within the module, and specimen management components for handling the egg during the incubation process. The incubation module may also employ AI/ML processes for automated measurement and testing, optimization, prediction, selection/ranking, and system configuration and control, and include robotic handling systems and advanced microscopy, imaging and optics systems, including computer and machine vision systems. In embodiments, the egg preparation module and the incubation module may work in tandem to ensure the eggs are properly prepared, handled, and incubated. The use of AI/ML processes in both modules automates these processes, reducing the potential for human error and increasing the efficiency and effectiveness of the IVF procedures, and the integration of these modules may allow for a streamlined and efficient process, from the initial preparation of the eggs to their incubation. This integration may be facilitated by the use of interconnected robotic IVF modules, which allow for the automated transfer of materials and data between the modules, ensuring that the eggs are handled and processed in a consistent and controlled manner necessary for the success of the IVF procedures.

In embodiments, as part of the imaging and AI/ML processes used to determine the egg's morphology and, for example the presence or absence of a polar body, a three-dimensional reconstruction model may be constructed to show the full physical entity of the oocyte, as opposed to being limited to, for example, a two-dimensional view obtained through a microscopic image. In an example, the three-dimensional view of the oocyte may be constructed through images taken from a plurality of angles of the oocyte, such as images made while physically moving the oocyte to obtain a view from multiple sides of the oocyte. Viewing multiple sides of the oocyte may be achieved by the egg preparation module by automatically manipulating the egg to view different sides of the oocyte, or it may be achieved by physically moving an imaging apparatus, such as a microscope, around a stationary oocyte. In another example, the three-dimensional view of the oocyte may be based at least in part on inferred data and predictive modeling of the oocyte. Such inference and predictive modeling may be based in part on prior data derived from egg imaging made by the IVF/ICSI platform. In an embodiment, optical coherence tomography (OCT), optical coherence microscopy (OCM), near-infrared light tomography, or some other technique may be used by the egg preparation module for oocyte imaging. OCT may be used by the IVF/ICSI platform to assess the maturity of oocytes. By providing three-dimensional images of the oocytes, OCT may identify the presence and position of the polar body, a structure that indicates the maturity of the egg. This information may be used to guide the ICSI process, as described herein, ensuring that the needle is introduced at the ideal position (as used herein, "insemination process," "insemination system," "insemination" and the like includes ICSI, IDEM on ICSI and all related ICSI systems, processes and protocols). In embodiments, the OCT system of the IVF/ICSI platform may be used in combination with the AI/ML system of the IVF/ICSI platform to take planar views of an oocyte throughout its development, allowing for more detailed tracking of its maturity, and be used to visualize multiple eggs simultaneously, providing a more efficient method of assessing egg maturity over traditional methods performed by human operators.

In embodiments, the egg preparation module may use polarized light and/or polarized sensitive OCT to automatically locate the presence or absence of a meiotic spindle and define best positioning of the oocyte during injection and to assess membrane integrity to allow identification of a successful injection. In embodiments, the maturity of the egg may be measured based at least in part by automatically identifying the meiotic spindle using imaging and AI/ML processes as described herein. In embodiments, meiotic spindle inspection may also be used to form a predictive algorithm for assisting in determining the probability of whether an egg is going to adequately mature, and when it might mature with further incubation.

In embodiments of the present disclosure, the egg preparation module may include egg retrieval components, systems, and processes. In embodiments of the present disclosure, the egg preparation module may include AI/ML for automated detection, identification, and classification. In embodiments of the present disclosure, the egg preparation module may include AI/ML for automated measurement and testing. In embodiments of the present disclosure, the egg preparation module may include AI/ML for optimization. In embodiments of the present disclosure, the egg preparation module may include AI/ML for prediction. In embodiments of the present disclosure, the egg preparation module may include AI/ML for selection/ranking. In embodiments of the present disclosure, the egg preparation module may include AI/ML for semi-autonomous, supervised, or autonomous robotics. In embodiments of the present disclosure, the egg preparation module may include AI/ML for system configuration and control. In embodiments of the present disclosure, the egg preparation module may include fully autonomous AI/ML. In embodiments of the present disclosure, the egg preparation module may include optical and machine vision components, systems, and processes. In embodiments of the present disclosure, the egg preparation module may include robotic handling systems and processes. In embodiments of the present disclosure, the egg preparation module may include sensor components, systems, and processes. In embodiments of the present disclosure, the egg preparation module may include specimen management components, systems, and processes. In embodiments of the present disclosure, the egg preparation module may include enzymatic oocyte denudation processes, systems and components. In embodiments of the present disclosure, the egg preparation module may include advanced microscopy systems and components.

The present disclosure provides an automated ICSI platform that uses robotics and AI/ML, including machine vision, to perform ICSI in an automated fashion. The system aims to enhance the consistency and success rate of ICSI procedures. The automated ICSI platform comprises both hardware and software components. The hardware includes an inverted microscope, a stage movement controller, cameras, micromanipulators, a laser objective, a motor controller, injectors, a piezoelectric actuator, microtool holders, and a 3D printed dish holder. The software components include software to operate the AI/ML, optics and the microscope and added devices. The system may operate by performing a sequence of pre-programmed processes, which may be initiated with a single command issued from a computer. The procedure may also be performed with multiple commands, each intended for a specific process in the procedure.

The person operating the computer may do so remotely and the manipulators and/or the microscope used throughout the process may be handled robotically. Imaging throughout the process may be visualized on a computer screen.

The IVF/ICSI platform may automate the ICSI procedure, including sperm preparation and immobilization, egg handling, zona pellucida ablation, oolemma breaking, sperm deposition, and egg release. The system may also provide controls for microscope focusing, pressure control in the pipettes, and movement of the stage and pipettes.

After the automated ICSI procedure, a human operator may remove the ICSI dish from the microscope stage, wash the eggs using manual pipetting, and place the eggs in culture in an incubator. Alternatively, these processes of removing the ICSI dish from the microscope stage, washing the eggs using pipetting, and placing the eggs in culture in an incubator may be performed automatically and robotically by the IVF/ICSI platform.

The disclosed system may provide a more consistent and reliable approach to ICSI. By automating these processes, the system may reduce variability, improve the success rate of ICSI procedures, and potentially increase the efficiency of ART.

In the context of ICSI, automation includes the use of robotics and AI/ML-assistance, as described herein, so that certain processes in the microinjection procedure that ordinarily require a highly skilled human operator are performed by an intelligent robotic system of the IVF/ICSI platform.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering or other labeling of instructions or method steps is done for convenient reference, not to indicate a fixed order.

Numerical terms, such as "first," "second," and "third," may be used in the disclosure and claims as unique labels: they are not used to imply a sequence or order unless the context clearly indicates otherwise. In other words, a "second" element could be relabeled as a "first" element without departing from the principles of the present disclosure. Further, the presence of a "second" element does not imply or require the presence of a "first" element. Similarly, the presence of a "first" element does not imply or require the presence of a "second" element.

Unless the context clearly indicates otherwise, the singular articles "a," "an," and "the" before a noun do not restrict the noun to a single instance. The verbs "comprise," "include," and "have" are inclusive and therefore specify the presence of elements without excluding the presence of one or more additional elements.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "coupled," "engaged," "adjacent," "next to," "on top of," "above," "below," and "disposed." Unless explicitly described as being "direct," when a relationship between first and second elements is described in the above disclosure, that relationship encompasses a direct relationship where no other intervening elements are present between the first and second elements as well as an indirect relationship where one or more intervening elements are present (either spatially or functionally) between the first and second elements.

The term "set" generally means a grouping of one or more elements. The elements of a set do not necessarily need to have any characteristics in common or otherwise belong together. However, in various implementations a "set" may, in certain circumstances, be the empty set (in other words, the set has zero elements in those circumstances). As an example, a set of search results resulting from a query may, depending on the query, be the empty set. In contexts where it is not otherwise clear, the term "non-empty set" can be used to explicitly denote exclusion of the empty set that is, a non-empty set will always have one or more elements.

A "subset" of a first set generally includes some of the elements of the first set. In various implementations, a subset of the first set is not necessarily a proper subset: in certain circumstances, the subset may be coextensive with (equal to) the first set (in other words, the subset may include the same elements as the first set). In contexts where it is not otherwise clear, the term "proper subset" can be used to explicitly denote that a subset of the first set must exclude at least one of the elements of the first set. Further, in various implementations, the term "subset" does not necessarily exclude the empty set. As an example, consider a set of candidates that was selected based on first criteria and a subset of the set of candidates that was selected based on second criteria; if no elements of the set of candidates met the second criteria, the subset may be the empty set. In contexts where it is not otherwise clear, the term "non-empty subset" can be used to explicitly denote exclusion of the empty set.

The phrase "at least one of A, B, and C" should be construed to mean a logical (A OR B OR C), using a non-exclusive logical OR, and should not be construed to mean "at least one of A, at least one of B, and at least one of C." The phrase "at least one of A, B, or C" should be construed to mean a logical (A OR B OR C), using a non-exclusive logical OR. The phrase "A, B, and/or C" should be construed in the same way as the phrase "at least one of A, B, and C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgments of, the information to element A.

In this application, including the definitions below, the term "module" can be replaced with the term "controller" or the term "circuit." In this application, the term "controller" can be replaced with the term "module." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); processor hardware (shared, dedicated, or group) that executes code; memory hardware (shared, dedicated, or group) that is coupled with the processor hardware and stores code executed by the processor hardware; other suitable hardware components that provide the described functionality; or a combination of some or all of the above, such as in a system-on-chip.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2018 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

Some or all hardware features of a module may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a module may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

The memory hardware may also store data together with or separate from the code. Shared memory hardware encompasses a single memory device that stores some or all code from multiple modules. One example of shared memory hardware may be level 1 cache on or near a microprocessor die, which may store code from multiple modules. Another example of shared memory hardware may be persistent storage, such as a solid state drive (SSD) or magnetic hard disk drive (HDD), which may store code from multiple modules. Group memory hardware encompasses a memory device that, in combination with other memory devices, stores some or all code from one or more modules. One example of group memory hardware is a storage area network (SAN), which may store code of a particular module across multiple physical devices. Another example of group memory hardware is random access memory of each of a set of servers that, in combination, store code of a particular module. The term memory hardware is a subset of the term computer-readable medium.

The apparatuses and methods described in this application may be partially or fully implemented by a special-purpose computer created by configuring a general-purpose computer to execute one or more particular functions embodied in computer programs. Such apparatuses and methods may be described as computerized or computer-implemented apparatuses and methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special-purpose computer, device drivers that interact with particular devices of the special-purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PUP (PHP: Hypertext Preprocessor), Scala, Eiffel, Smalltalk, Erlang, Ruby, Flash®, Visual Basic®, Lua, MATLAB, SIMULINK, and Python®.

The term non-transitory computer-readable medium does not encompass transitory electrical or electromagnetic signals propagating through a medium (such as on a carrier wave). Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

Various example embodiments of the invention are described in the following clauses.

Clause 1: A system for automated, artificial-intelligence-based oocyte identification and processing, the system comprising:

- an imaging system positioned in proximity to a biological sample containing a candidate cumulus-oocyte-complex (COC), wherein the imaging system is configured to identify and locate the candidate COC within the biological sample;
- a set of stations, wherein each station of the set of stations is configured to receive the biological sample;
- a set of robotic arms configured to:
  - move the biological sample between one or more stations of the set of stations, and
  - denude the candidate COC from the biological sample; and
- an artificial intelligence/machine learning system (AI/ML system) operatively coupled to at least one of: the imaging system, the set of robotic arms, or the set of stations.

Clause 2: The system of clause 1 wherein the imaging system includes:

- an upper imaging system positioned above the biological sample, and
- a lower imaging system positioned below the biological sample.

Clause 3: The system of clause 2 wherein the upper imaging system is configured to identify and locate the candidate COC within the biological sample.

Clause 4: The system of any of clauses 2-3 wherein the lower imaging system is configured to determine if the candidate COC is a COC by identifying a presence or absence of an oocyte within the candidate COC.

Clause 5: The system of clause 4 wherein:

- the lower imaging system includes an optical coherence tomography (OCT) imaging system, and
- the OCT imaging system is configured to determine if the candidate COC is a COC by identifying a presence or absence of an oocyte within the candidate COC.

Clause 6: The system of clause 5 wherein the OCT imaging system is configured to generate a three-dimensional (3D) image of the biological sample.

Clause 7: The system of any of clauses 5-6 wherein:

- the lower imaging system includes a microscopy system, and
- in response to the OCT imaging system identifying the presence of the oocyte within the candidate COC, the microscopy system is configured to determine a maturity of the oocyte.

Clause 8: The system of clause any of clauses 2-7 wherein the lower imaging system is moveable along a first track in a first direction and along a second track in a second direction.

Clause 9: The system of any of clauses 2-8 wherein the upper imaging system includes a set of cameras.

Clause 10: The system of any of clauses 1-9 wherein the biological sample includes a plurality of candidate COCs.

Clause 11: The system of any of clauses 1-10 wherein the set of robotic arms is configured to receive a tool.

Clause 12: The system of clause 11 wherein the tool includes a pipette.

Clause 13: The system of clause 12 wherein the pipette is configured to collect the biological sample.

Clause 14: The system of any of clauses 1-13 wherein the set of robotic arms includes a grabber configured to move a culture container between the set of stations.

Clause 15: The system of clause 14 wherein the biological sample is contained within the culture container.

Clause 16: The system of any of clauses 1-15 wherein the set of stations includes at least one of: an incubation station, a viewing station, or a working station.

Clause 17: The system of clause 16 wherein:

- the set of stations includes the incubation station, and
- the incubation station includes a first incubation station and a second incubation station.

Clause 18: The system of any of clauses 1-17 wherein the set of robotic arms includes a first robotic arm and a second robotic arm.

Clause 19: The system of any of clauses 1-18 wherein each robotic arm of the set of robotic arms is movable in six degrees of freedom.

Clause 20: The system of any of clauses 1-19 further comprising a transfer bay configured to receive the biological sample.

The invention claimed is:

1. A system for automated, artificial-intelligence-based oocyte identification and processing, the system comprising:

- an imaging system positioned in proximity to a biological sample containing a candidate cumulus-oocyte-complex (COC), wherein the imaging system:
  - is configured to identify and locate the candidate COC within the biological sample, and
  - includes an upper imaging system positioned above the biological sample and a lower imaging system positioned below the biological sample;
- a set of stations, wherein each station of the set of stations is configured to receive the biological sample;
- a set of robotic arms configured to:
  - move the biological sample between one or more stations of the set of stations, and
  - denude the candidate COC from the biological sample; and
- a control system configured to control at least one of: the imaging system, the set of robotic arms, or the set of stations.

2. The system of claim 1 wherein the upper imaging system is configured to identify and locate the candidate COC within the biological sample.

3. The system of claim 1 wherein the lower imaging system is configured to determine if the candidate COC is a COC by identifying a presence or absence of an oocyte within the candidate COC.

4. The system of claim 3 wherein:

- the lower imaging system includes an optical coherence tomography (OCT) imaging system, and
- the OCT imaging system is configured to determine if the candidate COC is a COC by identifying a presence or absence of an oocyte within the candidate COC.

5. The system of claim 4 wherein the OCT imaging system is configured to generate a three-dimensional (3D) image of the biological sample.

6. The system of claim 4 wherein:

the lower imaging system includes a microscopy system, and in response to the OCT imaging system identifying the presence of the oocyte within the candidate COC, the microscopy system is configured to determine a maturity of the oocyte.

7. The system of claim 1 wherein the lower imaging system is moveable along a first track in a first direction and along a second track in a second direction.

8. The system of claim 1 wherein the upper imaging system includes a set of cameras.

9. The system of claim 1 wherein the biological sample includes a plurality of candidate COCs.

10. The system of claim 1 wherein the set of robotic arms is configured to receive a pipette.

11. The system of claim 10 wherein the pipette is configured to collect the biological sample.

12. The system of claim 1 wherein the control system includes an artificial intelligence/machine learning system (AI/ML system).

13. The system of claim 1 wherein the set of robotic arms includes a grabber configured to move a culture container between the set of stations.

14. The system of claim 13 wherein the biological sample is contained within the culture container.

15. The system of claim 1 wherein the set of stations includes at least one of: an incubation station, a viewing station, or a working station.

16. The system of claim 15 wherein:

the set of stations includes the incubation station, and the incubation station includes a first incubation station and a second incubation station.

17. The system of claim 1 wherein the set of robotic arms includes a first robotic arm and a second robotic arm.

18. The system of claim 1 wherein each robotic arm of the set of robotic arms is movable in six degrees of freedom.

19. The system of claim 1 further comprising a transfer bay configured to receive the biological sample.

* * * * *